United States Patent
Freimuth

(10) Patent No.: US 7,157,266 B2
(45) Date of Patent: Jan. 2, 2007

(54) STRUCTURE OF ADENOVIRUS BOUND TO CELLULAR RECEPTOR CAR

(75) Inventor: Paul I. Freimuth, East Setauket, NY (US)

(73) Assignee: Brookhaven Science Associates LLC, Upton, NY (US)

( * ) Notice: Subject to any disclaimer, the term of this patent is extended or adjusted under 35 U.S.C. 154(b) by 450 days.

(21) Appl. No.: 10/218,419

(22) Filed: Aug. 14, 2002

(65) Prior Publication Data

US 2003/0077813 A1  Apr. 24, 2003

Related U.S. Application Data

(63) Continuation-in-part of application No. 09/389,603, filed on Sep. 3, 1999, now Pat. No. 6,737,234, which is a continuation-in-part of application No. 09/236,423, filed on Jan. 25, 1999, now Pat. No. 6,395,875.

(51) Int. Cl.
- *C12N 7/01* (2006.01)
- *C12N 7/04* (2006.01)
- *C12N 15/861* (2006.01)
- *A61K 48/00* (2006.01)
- *C12Q 1/70* (2006.01)

(52) U.S. Cl. .............................. 435/235.1; 435/320.1; 435/236

(58) Field of Classification Search ............. 435/235.1, 435/320.1, 69.1, 455, 456
See application file for complete search history.

(56) References Cited

U.S. PATENT DOCUMENTS

| 5,846,782 | A * | 12/1998 | Wickham et al. | 435/69.7 |
| 6,455,314 | B1 * | 9/2002 | Wickham et al. | 435/456 |
| 2002/0081280 | A1 * | 6/2002 | Curiel et al. | 424/93.2 |

OTHER PUBLICATIONS

Krasnykh et al., J. Virol., 1998, vol. 72, No. 3, pp. 1844-1852.*
U.S. Appl. No. 60/099,851.*
U.S. Appl. No. 60/136,529.*

* cited by examiner

*Primary Examiner*—David Guzo
(74) *Attorney, Agent, or Firm*—Lori-Anne Neiger

(57) ABSTRACT

Disclosed is a mutant CAR-DI-binding adenovirus which has a genome comprising one or more mutations in sequences which encode the fiber protein knob domain wherein the mutation causes the encoded viral particle to have a significantly weakened binding affinity for CAR-DI relative to wild-type adenovirus. Such mutations may be in sequences which encode either the AB loop, or the HI loop of the fiber protein knob domain. Specific residues and mutations are described. Also disclosed is a method for generating a mutant adenovirus which is characterized by a receptor binding affinity or specificity which differs substantially from wild type.

24 Claims, 4 Drawing Sheets

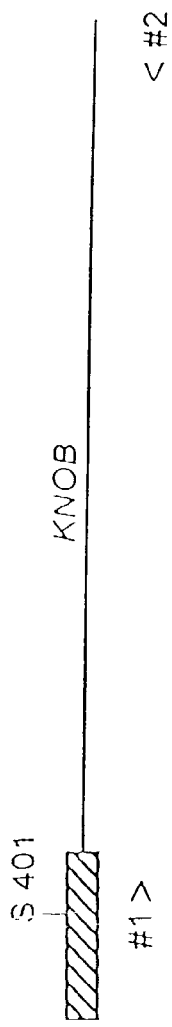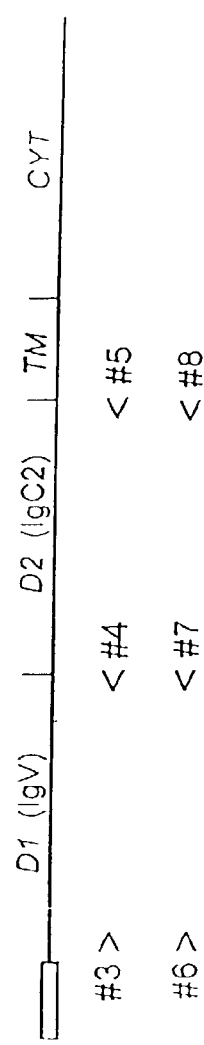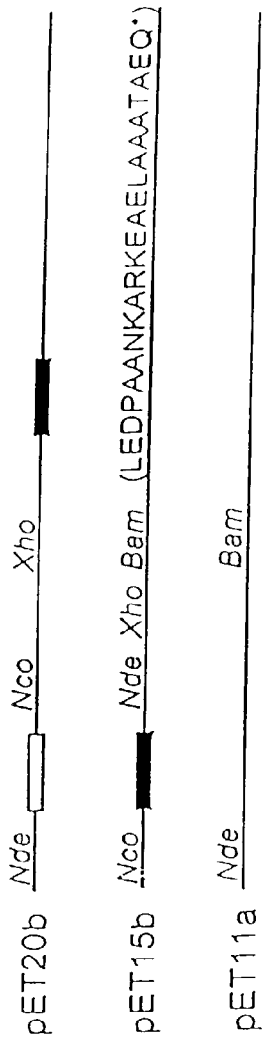

STRUCTURE OF ADENOVIRUS BOUND TO CELLULAR RECEPTOR CAR

The present application is a continuation-in-part of U.S. patent application Ser. No. 09/389,603 filed on Sep. 3, 1999, now U.S. Pat. No. 6,737,234, which was a continuation-in-part of U.S. patent application Ser. No. 09/236,423 filed on Jan. 25, 1999, now U.S. Pat. No. 6,395,875, and which are incorporated herein by reference.

This invention was made with Government support under contract number DE-AC02-98CH10886, awarded by the U.S. Department of Energy. The Government has certain rights in the invention.

BACKGROUND OF THE INVENTION

Characterization of the molecular basis for virus attachment to cells has importance both for understanding virus tropism and for developing agents that inhibit virus binding or alter the specificity of binding. Recently, a cellular receptor for adenovirus type 2 and other closely related serotypes was identified. This receptor, encoded by a single gene on human chromosome 21 (Mayr et al., *J. Virol.* 71: 412–8 (1997)), is a 46 kD glycoprotein which also serves as a receptor for group B coxsackieviruses (CBV) and thus was termed the coxsackievirus and adenovirus receptor (CAR). CAR mRNA is present in many human tissues. A broad tissue distribution of CAR protein expression correlates with the broad tropism of CBV, but subgroup C adenoviruses that are known to bind CAR have a much more restricted tropism limited primarily to the upper respiratory tract. Thus, other factors in addition to receptor availability clearly have important roles in determining adenovirus tropism. Although adenovirus binds to CAR with high affinity (Mayr et al., *J. Virol.* 71: 412–8 (1997); Wickham et al., *Cell.* 73: 309–19 (1993)), virus titers are significantly reduced on cells with down-regulated CAR expression (Freimuth, P., *J. Virol.* 70: 4081–5 (1996)). These results suggest that adenovirus infection in vivo may be restricted to cells which express CAR at levels above a minimum threshold concentration. CAR protein levels are relatively low on the apical surface of differentiated (ciliated) respiratory epithelial cell cultures, which may account for the poor efficiency of adenoviral gene transfer to human lung tissue in vivo.

Adenovirus binding to CAR results from an interaction between rod-shaped proteins located at the capsid vertices, called viral fibers, and the extracellular region of CAR. The monomers of this homotrimeric fiber protein range in size from 30 to 65 kDa depending on the serotype (Huang et al., *J. Virol.* 73: 2798–2802 (1999)). They are composed of a conserved amino terminal tail that mediates their interaction with the penton base, a variable-length elongated (shaft) domain, and a carboxyl-terminal globular domain, termed the knob, which mediates the high-affinity interaction with its cellular receptor. The knob domain of adenovirus type 5 (Ad5) was expressed in *E. coli* as a soluble, trimeric, biologically active protein, and its 3-dimensional structure was determined by x-ray crystallography (Xia et al., *Structure* 2: 1259–70 (1994)).

The predicted amino acid sequence of CAR suggests a structure consisting of two extracellular domains related to the immunoglobulin IgV and IgC2 domain folds (Bork et al., *J. Mol Biol.* 242: 309–20 (1994); Bergelson et al., *Science* 275: 1320–3 (1997); Tomko et al., *Proc. Natl. Acad. Sci. USA* 94: 3352–6 (1997)), a single membrane-spanning region, and one carboxy-terminal cytoplasmic domain. Regions of CAR necessary for binding the fiber knob domain have not yet been determined.

SUMMARY OF THE INVENTION

The present invention relates to a mutant adenovirus which has a genome comprising one or more mutations in sequences which encode the fiber protein knob domain, the viral particle encoded by the genome being characterized by a significantly weakened binding affinity for CAR-D1 relative to wild-type adenovirus. The mutant adenovirus may be a CAR-D1-binding adenovirus of subgroup A, C, D, E and the long fiber of F (FL). Preferably, the mutant adenovirus is a mutant CAR-D1-binding adenovirus of subgroup A or C. More preferably, the mutant adenovirus is adenovirus serotype 2 or serotype 5, of subgroup C. The mutation may be in sequences which encode the AB loop of the fiber protein knob domain. Specific residues and mutations are described. Alternatively, the mutations which cause significantly weakened binding affinity for CAR-D1 may be in sequences which encode the HI loop of the fiber protein knob domain of the encoded viral particle. Specific residues and mutations are described.

Another aspect of the present invention is a method for generating a mutant adenovirus which is characterized by a receptor binding affinity or specificity which differs substantially from wild type and which is significantly weakened for CAR-D1. This method is performed on adenoviruses which bind CAR-D1. Residues of the adenovirus fiber protein knob domain of the adenovirus, which are predicted to alter D1 binding when mutated, are identified from the crystal structure coordinates of the AD12knob:CAR-D1 complex. A mutation which alters one or more of the identified residues is introduced into the genome of the adenovirus, and whether or not the mutant produced exhibits altered adenovirus-CAR binding properties is determined. This method can be used to produce a mutant adenovirus which, under physiological conditions, has significantly weakened binding affinity for CAR-D1 relative to wild type adenovirus or which binds a receptor other than CAR-D1, including an engineered receptor. The introduced mutation may result in an amino acid substitution, an amino acid deletion, an amino acid insertion in the encoded viral particle or combinations thereof. Introduced mutations may serve to alter the conformation of one or more residues of knob which participate directly in D1 binding. Such residues include residues of the AB loop, the CD loop, the DE loop, the FG loop, the E strand and the F strand. Alternatively, the mutation may be introduced in a codon encoding the residue of knob which participates directly in D1 binding. Specific residues in the AB loop, the CD loop, the FG loop, the E strand, the F strand, and the DE loop which participate directly in binding are identified.

Another aspect of the present invention is a method for identifying an inhibitor of adenovirus binding to CAR. In the method, a three-dimensional structure derived by X-ray diffraction from a crystal of adenovirus knob trimer bound to CAR-D1 is provided and then employed to design or select a potential inhibitor. The potential inhibitor is synthesized and then whether or not the potential inhibitor inhibits adenovirus binding to CAR is determined. The crystal of the Ad12knob:CAR-D1 complex which is used in the method preferably has $P4_332$ space group symmetry with a cubic unit cell with 167.85 angstroms per side. Atomic coordinates are preferably obtained by means of computational analysis. A set of atomic coordinates which define the three dimensional structure are provided. In one embodiment, the potential inhibitor is designed to interact non-covalently with one or more residues of the adenovirus fiber knob protein domain. In another embodiment, the potential inhibitor is designed to interact non-covalently with one or more residues of CAR-D1. Specific residues for covalent and non-covalent interaction are listed. In another embodiment, the potential inhibitor is designed to interact non-covalently with residues which line a cavity formed during adenovirus knob trimer/CAR-D1 binding. The potential inhibitor can be designed by identifying chemical entities or fragments capable of associating with the adenovirus knob trimer, and assembling the identified chemical entities or fragments into a single molecule to provide the structure of said potential inhibitor. Such an inhibitor may be designed de novo or from a known inhibitor. Mechanisms of inhibition include competitive inhibition, non-competitive inhibition and uncompetitive inhibition.

BRIEF DESCRIPTION OF THE DRAWINGS

FIG. 1 is a diagrammatic representation of the Ad12 fiber knob and the extracellular domains of human CAR. a) The Ad12 knob domain (solid line) begins at a conserved motif (amino acids 409–412) and extends to the fiber protein carboxy terminus (Glu 587) (corresponding to nucleotides 30592–31128 of GenBank Accession #X73487). A fragment of Ad12 DNA encoding the entire knob domain and several amino acids from the preceding fiber shaft region (hatched box) was amplified by PCR using forward primer #1 and reverse primer #2. The resulting PCR product was cloned between the NdeI and BamHI sites of pET15b. b) The human CAR protein consists of a N-terminal signal peptide (open box), two extracellular Ig-related domains (D1, D2), a membrane spanning region (TM) and a cytoplasmic domain (CYT). cDNA fragments encoding D1 and D1/D2 were amplified by PCR using forward primer #3 and reverse primers #4 and #5. The resulting PCR products were cloned between the NcoI and XhoI sites of pET20b. Similar D1- and D1/D2-encoding cDNA fragments were amplified by PCR using forward primer #6 and reverse primers #7 and #8. The resulting PCR products were cloned between the NdeI and BamHI sites of pET15b. The NcoI-XhoI fragments were transferred from pET20b into pET15b, a manipulation which resulted in the fusion of the genes in frame to pET15b vector DNA encoding a 22 amino acid extension at the carboxy-terminus. c) pET vectors for protein expression in E. coli. The open and filled boxes represent bacterial signal peptides and hexahistidine tags, respectively. The restriction sites used in this study are shown, and the sequence of the pET15b-encoded 22 amino acid (SEQ ID NO: 1) carboxy-terminal extension of the soluble CAR-D1 domain (sD1) is indicated in single letter code.

DETAILED DESCRIPTION OF THE INVENTION

Figure 2:
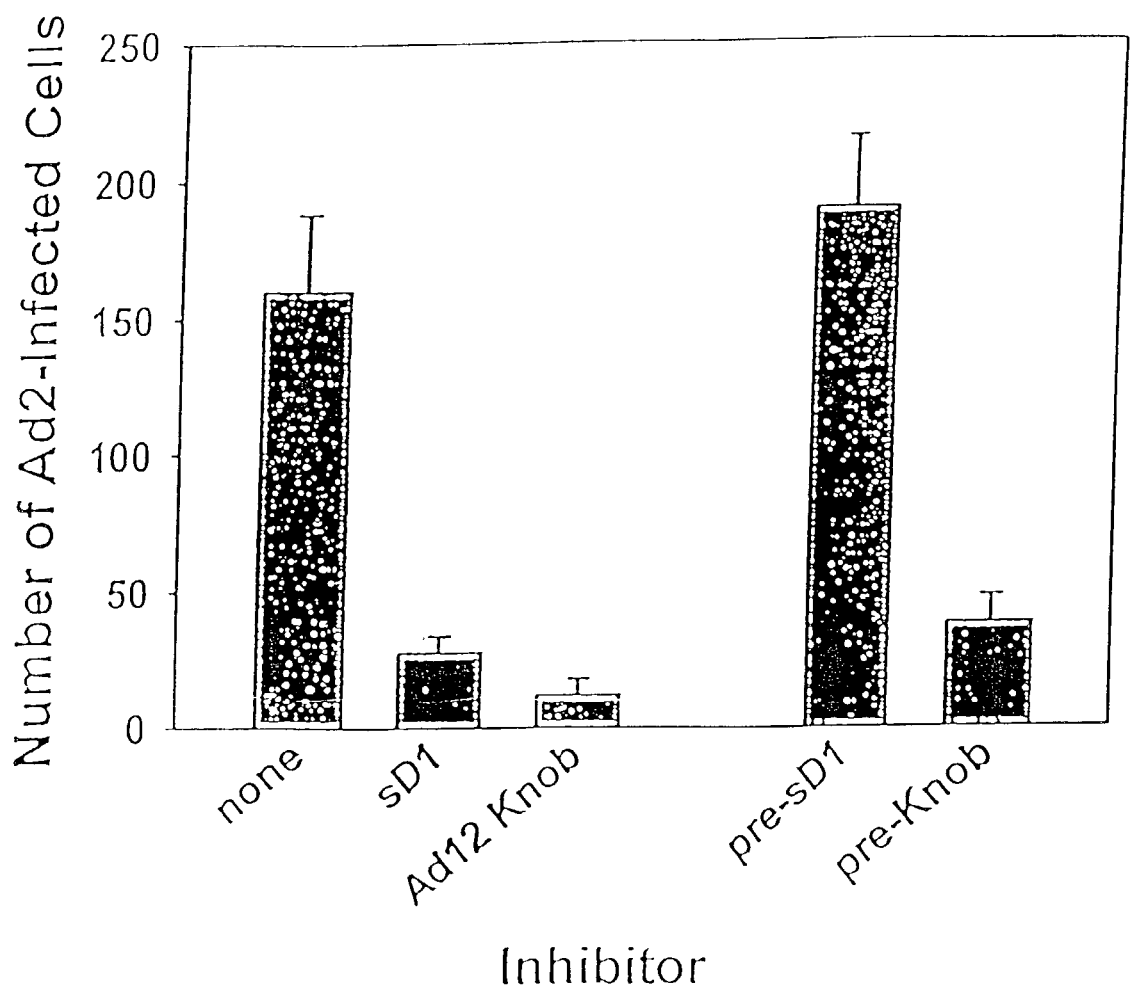
FIG. 2 is a diagrammatic representation of results from experiments measuring the ability of sD1 and Ad12 knob to prevent infection of cells by Ad2. HeLa cell monolayers were infected with about 200 focus-forming units (FFU) per well of Ad2 virus in the presence or absence of sD1 or Ad12 knob. The number of infected cells that resulted is shown (mean±SD). Control cultures were pretreated with sD1 and knob (pre-sD1, pre-Knob) and then washed prior to infection to remove the added sD1 and any unbound Ad12 knob.

The present invention is based, in one aspect, on the discovery that the adenovirus-binding activity of human CAR is localized in the amino-terminal IgV-related domain. As detailed in the Exemplification section, the isolated amino-terminal IgV-related domain of CAR (referred to herein as D1 or CAR-D1) and the entire extracellular region (referred to herein as D1/D2 or CAR-D1/D2) both have the ability to form complexes with Ad12 knob. Furthermore, the presence of free D1 in soluble form, inhibits Ad2 virus infection of HeLa cells and the presence of free Ad12 fiber knob also inhibits Ad2 virus infection of HeLa cells. Collectively, these observations indicate that D1 is the component of CAR responsible for the adenovirus-binding activity for adenoviruses of subgroups A and C.

One embodiment of the present invention is an isolated polypeptide that binds adenovirus comprising an amino acid sequence corresponding to the D1 domain of the human CAR protein. The preferred embodiment is an isolated polypeptide comprising residues 20–144 of the pre-CAR sequence (GenBank Accession #Y07593), with the amino acid substitutions of L20M and S21G, generated to facilitate cloning. The wild type sequence comprising residues 20–144 of pre-CAR also binds adenovirus, as does a polypeptide sequence comprising residues 20–144 of the pre-CAR sequence which contains one or more conservative amino acid substitutions.

Another embodiment of the present invention is an isolated polypeptide comprising an amino acid sequence corresponding to the D1 and D2 domains of the human CAR protein. D1 and D2 are IgV and IgC2 domains and constitute the entire extracellular region of the human CAR protein. The D1/D2 polypeptide demonstrates analogous viral binding activity to the D1 polypeptide described above. The preferred embodiment comprises the amino acid sequence corresponding to residues 20–237 of the human pre-CAR protein (GenBank Accession #Y07593), with two amino acid substitutions of L20M and S21G, generated to facilitate cloning. The wild type sequence comprising residues 20–237 of pre-CAR also binds adenovirus, as does a polypeptide sequence comprising residues 20–237 of the pre-CAR sequence which contains one or more conservative amino acid substitutions.

Another aspect of the present invention is the recombinant DNA molecule that encodes the above described polypeptides. One embodiment is a recombinant DNA molecule comprising a DNA sequence encoding the adenovirus binding domain, D1, of the CAR protein. In the preferred embodiment, this sequence corresponds to nucleotide 121 to 493 of the human CAR cDNA (GenBank Accession #Y07593). Another embodiment is the recombinant DNA molecule comprising the entire extracellular region, D1 and D2, of the CAR protein. In the preferred embodiment, this DNA sequence corresponds to nucleotide 121 to 770 of the human CAR cDNA sequence (GenBank Accession #Y07593).

The isolated polypeptides of the present invention can be produced in vitro by inserting the corresponding recombinant DNA molecules described above into an expression vector (e.g. a prokaryotic or eukaryotic expression vector). Such vectors contain all necessary regulatory signals to promote the expression of a DNA sequence of interest. The use of such vectors is a matter of routine experimentation for one of average skill in the art. The expression vector with the inserted DNA sequence of the present invention is then introduced into an appropriate cell under conditions favorable for expression. In the preferred embodiment, the cell is prokaryotic and is a bacteria cell. However, the proteins can also be expressed in eukaryotic cells by similar methods, utilizing eukaryotic expression vectors. Such cells can be used to study the biological properties of the protein in a controlled cell system or, alternatively, for the purpose of protein production and purification.

Isolation of the above proteins from the bacteria is achieved through routine purification procedures. In one embodiment, the CAR coding sequences are engineered downstream of sequences encoding hexahistidine, to produce the CAR fragment with an N-terminal hexahistidine tag. As described in the Exemplification section of this application, the D1 and D1/D2 polypeptides produced by this method are insoluble when generated in *E. coli*. However, functional products are obtained when the polypeptides are refolded from urea-solubilized inclusion bodies and purified by anion exchange chromatography. Following purification, the tag is optionally cleaved off by digestion with thrombin to yield the intact CAR fragment.

In the preferred embodiment, the D1 polypeptide is expressed in the form of a fusion protein which results in the production of D1 domain that is soluble and functional when expressed in *E. coli* at 18° C. As described in the Exemplification section of the present application, D1 engineered to have a short C-terminal amino acid extension is partially soluble when expressed in *E. coli*, and also retains virus-binding activity. Without being bound by theory, the fused extension is thought to enable the IgV domain to fold into a soluble structure within *E. coli* cells. Functional, soluble D1 isolated in this manner is preferred for use over D1 which is produced as insoluble in *E. coli* and resolubilized because resolubilized proteins can contain non-functional structural isomers.

The fusion protein is generated by expression from a recombinant DNA molecule containing the D1 polypeptide coding sequence, described above, fused in frame to a DNA sequence encoding a polypeptide sequence which facilitates folding of the D1 polypeptide into a functional, soluble domain. This recombinant DNA molecule is then inserted into a prokaryotic expression vector which is then transformed into a bacteria cell, under conditions appropriate for expression. In one embodiment the fusion is downstream, resulting in a C-terminal extension. In the preferred embodiment, the D1 coding sequence is fused in frame to a downstream DNA sequence encoding the 22 residue polypeptide LEDPAANKARKEAELAAATAEQ (SEQ ID NO: 1) to generate a C-terminal extension. The isolated polypeptide that results from expression of this fused sequence comprises an amino acid sequence corresponding to amino acids 20–144 of human pre-CAR protein, and is herein referred to as sD1.

The present invention is also based, in part, on the discovery that free sD1 polypeptide functions as an antiviral agent by inhibiting viral infection of a cell. Results presented in the Exemplification section of this application indicate that free sD1 functions to inhibit cell infection by viruses that bind D1 of human CAR. As detailed in the Exemplification, both Ad2 and Ad12 (representative of adenovirus subgroup C and A, respectively) bind D1. These results, combined with the earlier observation that adenovirus competes for cell binding sites with a subgroup B coxsackievirus, indicate that members of coxsackievirus subgroup B also bind D1 (Lonberg-Holm et al., *Nature* 259: 679–81 (1976); Bergelson et al., *Science* 275: 1320–3 (1997); Tomko et al., *Proc. Natl. Acad. Sci. USA* 94: 3352–6 (1997)).

One embodiment of the present invention is a method for the treatment of a patient infected with a virus characterized as binding D1 with human CAR protein. The method comprises providing a therapeutic composition of D1 polypeptide and administering it to the patient. This method can be used to treat any viral infection involving a viral agent that binds to D1 including, but not limited to, adenovirus subgroup A, adenovirus subgroup C, and coxsackievirus subgroup B.

Effective therapeutic compositions will provide a sufficient amount of D1 polypeptide to affect binding of the virus to the extent that progression or spread of the infection is inhibited. In the preferred embodiment, the therapeutic composition comprises the D1 polypeptide in a stable, soluble form. For effective therapy, administration of the composition is targeted to the infected area, preferably through topical administration to a localized infection. Adenoviruses commonly infect the upper respiratory tract, the ocular region, and the gastrointestinal tract, whereas CBV has a broad tissue tropism. A therapeutic composition may take the form of eyedrops, an inhalant fluid, or an ingestible composition, for the treatment of an ocular, upper respiratory, or gastrointestinal infection, respectively.

The present invention also encompasses several other methods that utilize the above described compositions. In addition to using D1 polypeptide directly in the therapeutic treatment of viral infection, the isolated polypeptide can be exploited experimentally to identify and characterize molecules which bind CAR through the D1 domain, to study the infection process, and to develop new therapeutics. One such embodiment is a method of identifying molecules and portions thereof involved in binding to CAR through the D1 domain.

Experiments presented in the Exemplification section of this application indicate that CAR is bound by adenovirus-encoded proteins involved in cellular attachment. Evidence indicates that other viruses also bind CAR at the D1 domain in the infection process. In addition to this role as a receptor in viral infection, CAR is likely bound by a natural ligand in a healthy individual. Identification of D1 as the domain through which viruses attach to CAR, allows its use in binding assays in the identification and further characterization of these molecules.

Various binding assays can be used to identify and characterize D1 binding molecules. In vitro binding assays yield highly quantitative binding data, and have the advantage of being performed under extremely controlled conditions. In vivo binding assays are performed under physiological conditions and, while often more qualitative than quantitative, can provide physiologically relevant data.

In one embodiment, the molecule which binds D1 is an adenovirus knob protein. Presumably, the residues of knob that form the interface with CAR are conserved in adenovirus serotypes which bind to CAR, but are not conserved in serotypes which do not bind to CAR. The Ad2, representative of subgroup C, and Ad12, representative of subgroup A, knob amino acid sequences are only 43% identical, yet both viruses use CAR as the major attachment receptor and, as shown in the Exemplification section, Ad12 fiber can inhibit the infection of HeLa cells by Ad2. The importance of these conserved amino acids to CAR binding are readily testable using the polypeptide sequences disclosed in the present application. Along the same lines, evidence indicates that subgroup B adenovirus (e.g. types 3 and 7) do not bind the same cell receptors as subgroup A and C (Defer et al., *J Virol.* 64: 3661–73 (1990)). Regions of subgroup B and C knob sequences that differ radically may define receptor binding specificity (Xia et al., *Structure.* 2: 1259–70 (1994)).

In the preferred embodiment, an in vitro binding assay system is used to determine if alterations in viral knob proteins affect binding to D1 or D1/D2 polypeptides. These alterations include truncations and internal deletions of D1 binding knob proteins. Additionally, chimeras of D1 binding and non-D1 binding knob proteins can be tested for D1 binding, to determine the influence of defined knob protein regions on binding specificity. As experiments progress, subtle alterations made in the identified binding regions (e.g. amino acid substitutions) will define the residues involved in D1 binding. One of average skill in the art will recognize that the results of such studies can be applied to the production of recombinant adenovirus knob proteins and/or D1 proteins that possess distinct binding specificities.

Identification of D1 as the virus binding fragment also facilitates structural determination of the virus attachment proteins (e.g. Ad 12 knob, complexed to D1 or D1/D2). Such studies facilitate the identification of residues that form the receptor-knob interface.

The methods used in the study of knob binding are equally applicable to identifying molecules and portions thereof involved in the attachment of viruses other than adenovirus (e.g. coxsackievirus and natural ligands to CAR). One of skill in the art will recognize that information gathered from binding studies will usefully contribute to related applications of the present invention.

The compositions of the present invention can also be used in binding assays to screen for antiviral compounds which interfere specifically with the interaction between the D1 polypeptide of the human CAR protein and a viral attachment protein which binds to the D1 polypeptide. The demonstrated binding of D1 to viral attachment proteins, as detailed in the Exemplification, can be used as an assay for a primary step in virus infection. Compounds found to interfere with viral binding will have valuable therapeutic and experimental potential as antiviral agents.

In one embodiment, purified viral attachment protein is contacted with purified sD1 in an in vitro binding assay (e.g. ELISA type) in the presence and absence of a candidate compound. Decreased binding of D1 to the viral protein indicates the compound possesses anti-viral properties. Both in vitro and in vivo binding assays utilizing various detection methods can be used in such a screen. The performance of such binding assays is within the capabilities of one of average skill in the art. In the preferred embodiment, the viral attachment protein used in the screen is an adenovirus knob protein (e.g. Ad2 or Ad12).

The present invention also provides methods to specifically target a cell for viral infection by redirecting viral binding to a predetermined surface protein of the targeted cell. This can be accomplished by using a D1 containing adaptor bridge which binds to the virus and also binds to the surface protein. Because adenovirus infection in vivo is restricted to cells which express CAR at levels above a minimum threshold concentration, the use of a highly expressed surface protein is expected to produce a higher rate of infection of the target cell than will a less prevalent surface protein. In one embodiment, the adaptor bridge is generated by fusing D1 to single chain antibodies directed towards antigens expressed on the target cells (e.g. tumor cells). The virus is then contacted with the adaptor bridge under conditions appropriate for binding of the virus to the D1 portion of the adaptor bridge, to produce a virus-adaptor bridge complex. The target cell is then contacted with the virus-adaptor bridge complex under conditions appropriate for binding of the antibody portion of the adaptor bridge to the target cell. Contact of the virus-adaptor bridge complex with the target cell can take place via topical application or systemic administration. Upon binding of the virus-adaptor bridge complex to the target protein, the target cell becomes susceptible to infection by the attached virus. In one embodiment, the virus is an adenovirus. However, the virus can be any virus that binds D1, including a virus modified for therapeutic purposes (e.g. by recombinant engineering).

Adenovirus-based DNA expression vectors and delivery systems are highly utilized systems for gene delivery into animal cells, including in vitro cell culture and in vivo delivery (e.g. gene therapy). The use of specific targeting of adenoviruses allows the development of either a wider spectrum of target cells or conversely a narrower range of delivery, the latter improvement being beneficial to therapies such as chemotherapy aimed at specific elimination of diseased tissue. One skilled in the art can envision how information gathered in the above experiments regarding the binding sites involved in Adenovirus binding to D1 can be exploited for therapeutic purposes to generate recombinant adenovirus and D1 with highly specific binding recognition.

The present invention also provides methods for treating a patient with an infection caused by a virus that binds to human CAR. Experiments detailed in the Exemplification indicate that free Ad12 knob inhibits infection of HeLa cells by Ad2 virus. These observations indicate that free adenovirus Ad12 knob protein administered in a therapeutic composition can prevent the spread of an infection resulting from a virus that binds D1. The preparation and administration of effective therapeutic compositions comprising the Ad 12 knob protein are similar to that described above for D1.

Other aspects of the present invention relate to the three-dimensional structure of the fiber knob protein domain of Adenovirus serotype 12 (referred to herein as Ad12 knob) alone and in complex with the isolated and purified D1 domain of CAR, provided by Applicants. The structure coordinates of the Ad12 knob and the complex of Ad12 knob and CAR-D1 are deposited in the Protein Data Bank, access identification numbers 1NOB and 1KAC respectively. The term "structure coordinates" refers to mathematical coordinates derived from mathematical equations related to the patterns obtained on diffraction of a monochromatic beam of X-rays by the atoms (scattering centers) of the molecule or molecular complex in crystal form. The diffraction data obtained are used to calculate an electron density map of the repeating unit of the crystal. The electron density maps are used to establish the positions of the individual atoms within the unit cell of the crystal. Those of skill in the art understand that a set of structure coordinates determined by X-ray crystallography is not without standard error.

The structure coordinates provided herein may be modified from the original set by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates, and any combination thereof.

Structural analysis presented in Section II of the Exemplification below was used to identify the CAR binding site on Ad12 knob and specific residues in Ad12 knob and CAR-D1 which directly interact. Regions of Ad12 knob identified as directly involved in CAR-D1 binding are the AB loop, the carboxyl ends of the DE loop, the F strand and the FG loop. The Ad12knob:CAR-D1 complex forms without a significant conformational change in the knob domain, and buries a large mixed hydrophilic/hydrophobic surface area involving several non-contiguous loops of Ad12 knob and the β-strands on one face of CAR-D1, creating two buried cavities totaling approximately 120 $Å^3$. Structure based mutational analysis presented below supports the structural model deduced from this analysis.

One aspect of the present invention is a mutant adenovirus having a genome comprising one or more mutations in sequences which encode regions of the fiber protein knob domain specifically involved in binding of adenovirus to CAR-D1. The mutant viral particle encoded by the mutated genome is characterized by a significantly weakened binding affinity for CAR-D1 relative to the CAR-D1 binding affinity of wild-type adenovirus. A significantly weakened binding affinity for CAR-D1 is defined herein as a reproducibly lower binding affinity for CAR-D1 compared to wild type as determined by binding assays known in the art. A mutant adenovirus with undetectable binding affinity for CAR-D1 is also considered to have a weakened binding affinity for CAR-D1, the affinity being so minimal as to be undetectable. Weakened binding affinity as used herein may also include a coincident gain of binding affinity for another receptor molecule, as compared to wild-type adenovirus. The term receptor, as used herein, refers to any molecule which a virus binds to gain entry into a cell.

Using the structural data provided in the Exemplification section below several mutants of Ad12 which have significantly weakened binding affinity for CAR-D1 have been generated. One of skill in the art will recognize that mutations analogous to those identified in Ad12, can be generated in any serotype which binds CAR-D1 to produce a similar weakened binding affinity for CAR-D1 in the encoded virion relative to wild type. As such, the present invention is intended to encompass all adenovirus serotypes which bind CAR-D1. The specific mutation in another CAR-D1 binding serotype can be generated by one of skill in the art through no more than routine experimentation by examination of the amino acid sequence homology of Ad12 knob versus other CAR-D1-binding serotypes. This is particularly feasible for CAR-D1-binding serotypes having homologous sequences in the regions of the knob protein shown herein to participate in CAR-D1 binding, such as the AB loop.

Many of the mutants produced have one or more mutations in sequences which encode the AB loop. The AB loop of knob contributes over 50% of the interfacial interactions with D1, and is one of the identified candidate regions for mutagenesis affecting receptor binding. Specific positions identified for mutagenesis include position 417 and 418 of Ad12. Mutations at one or both of these positions results in weakened binding affinity for CARD1. Examples of specific mutations at these positions identified as inhibiting D1 binding are the substitution mutations P417E and P418A. In addition to substitution mutations, insertion and deletions at sites within the AB loop also lead to altered receptor binding affinity. For example, insertion of two amino acids, threonine and isoleucine, between residue 421 and 422 of Ad12 results in reduced CARD binding. Deletion of 425 and L426 of Ad12 also reduces CAR-D1 binding.

Other mutant adenoviruses with reduced CAR-D1 binding have been generated from mutations in the HI loop of knob. The concurrent deletion of amino acid G550 and I551 of AD12 results in reduced CAR-D1 binding.

Mutants of adenovirus serotypes currently being used for gene transfer vectors have particular value as a therapeutic tool.

CAR-D1 binding mutants of the present invention can be engineered to function as vectors for gene therapy. Recently, human adenovirus serotypes 2 and 5 have been adapted for use as vectors for efficient introduction of genes in vivo (Trapnell et al., *Current Opinion Biotech.* 5: 617–625 (1994); Acsadi et al., *J. Mol. Med.* 73: 165–180 (1995)). The adapted viruses are usually disabled (i.e. unable to propagate under natural conditions) in order to reduce the risk of transmission of the gene therapy vector from patients to the general population. Adenovirus vectors currently available for use in gene therapy and methods of producing the vectors are described by Massie et al., U.S. Pat. No. 5,891,690 (1999); Armentano et al., U.S. Pat. No. 5,824,544 (1998); Armentano et al., U.S. Pat. No. 5,707,618 (1998); Hammond et al., U.S. Pat. No. 5,792,453 (1998); the contents of which are incorporated herein by reference. Despite these advances, concern remains regarding the possible appearance of revertants which become replication competent through recombination with adenovirus sequences naturally present in a host recipient. Generation and use of Adenovirus type 2 and type 5 CAR-D1 binding mutants of the present invention in the form of vectors for gene therapy will provide an extra measure of control against possible transmission of a therapeutic mutant from patients to the general population.

Because the introduced mutations will also block the efficiency of gene transfer through CAR-mediated infection, it may be beneficial to introduce the gene delivery vectors of the present invention into the host cell by an alternate method. For instance, the viral vector can be further engineered to bind receptors other than CAR for cellular entry. Currently research is underway to develop laboratory strains of adenovirus which infect cells through novel receptors other than CAR to direct therapeutic adenovirus infection (e.g. a gene delivery vector) to specific target cells. Successful results have been achieved using bi-specific antibodies, where one arm of the antibody binds some component of the virus surface and the other arm binds to a molecule on the cell surface. Recombinant adenoviral gene delivery vectors which are similarly adapted to infect via alternate receptors to confer tissue specificity and methods for their generation have been described by Wickham et al., U.S. Pat. No. 5,559,099 (1996); Wickham et al., U.S. Pat. No. 5,770,442 (1998); Wickam et al., U.S. Pat. No. 5,731,190 (1998); the contents of which are incorporated herein by reference. Adenovirus mutants of the present invention can be generated by one of skill in the art to produce similar tissue or cell type specific delivery vectors.

Ideally, an adenovirus mutant of the present invention has a significantly weakened binding affinity for CAR-D1 such that it can be propagated efficiently under laboratory conditions, but not in natural infections in humans. Such a mutant would be particularly useful as a gene therapy vector.

Another aspect of the present invention is a method for generating a mutant adenovirus which is characterized by a receptor binding affinity or specificity which differs substantially from wild type. This method is applicable to adenovirus serotypes and mutants thereof which bind CAR-D1. Generally the method will be used to produce a mutant which has a reduced affinity for CAR-D1 relative to that of wild type. Similarly, a mutant which binds a receptor other than CAR-D1 may also be produced from a wild type virus.

The Exemplification below demonstrates by example that the findings regarding the structural interactions of Ad12 knob with CAR-D1 are readily applicable for generating adenovirus mutants which have altered receptor binding properties. Specifically, the information regarding the Ad12knob:CAR-D1 complex provided in the Exemplification section below, allows identification of residues of the adenovirus fiber protein knob domain which when mutated are predicted to alter D1 binding. Upon identification of one or more of these residues, a mutation is introduced into the genome of the adenovirus which alters one or more of the identified residues. The mutant which is produced from expression of the mutated genome is then tested in order to determine that the mutant exhibits altered adenovirus-CAR binding properties.

Residues of knob which when mutated are predicted to alter the binding properties of the virus when mutated include residues which are involved, either directly or indirectly, in D1 binding. Examples of amino acids which are directly involved with binding include, without limitation, residues which make contact with the receptor, and also residues which line or define binding sites. Residues directly involved in D1 binding also include residues which contribute directly to the topological mismatches in the interface with D1 which result in the formation of cavities upon binding. Because these cavities are thought to stabilize the complex, alteration of one or more residues which line or define these cavities is expected to alter knob/D1 binding.

Specific regions of Ad12 identified as containing residues which participate directly in D1 binding include without limitation the AB loop, the CD loop, the FG loop, the E strand and the F strand. Residues in the AB loop involved in binding include without limitation residues 409, 415, 417, 418, 419, 426, and 429 of Ad12. Residues in the CD loop involved in binding include without limitation residues 450 and 451. Residues in the FG loop involved in binding include without limitation residues 517, 519, 520 and 523. Residues in the E strand involved in binding include without limitation residue 494. Residues in the F strand involved in binding include without limitation residues 497 and 498. In addition, residue 487, which is in the DE loop, preceding strand E, was also identified as participating directly in D1 binding. The homologous residues can be identified in other adenovirus serotypes which bind CAR-D1 through examination of the sequence homology between the respective knob domains of the relevant viruses. This is particularly feasible for adenoviruse type 2 and type 5 which share considerable amino acid sequence homology with Ad12 in the AB loop.

Amino acids which have indirect involvement influence residues which are directly involved. Examples include, without limitation, residues adjacent or near directly involved residues. Proximity need not be limited to primary sequence, but may be from secondary or tertiary structural relationships. In addition, residues may be located near directly involved residues due to the formation of intermolecular complexes by knob monomers. The influence that indirectly involved amino acids have on directly involved amino acids may be steric, chemical, or a combination effects. Indirectly involved amino acids also include residues which participate in defining an element of the protein structure which is crucial for receptor binding (e.g. the necessary conformation of a protein or the ability to form intermolecular complexes).

Importantly, amino acids which are not significantly involved (directly or indirectly) in receptor binding of the unmutated adenovirus, may assume a role (direct or indirect) in receptor binding through mutagenesis. The term "unmutated adenovirus" as used herein refers to the original sequence prior to a specific round of mutagenesis, the term being inclusive of wild type sequences as well as previously altered sequences. Mutagenesis which confers a role in function to a previously uninvolved residue commonly involves the substitution of another amino acid at that particular position. However, a new role in function may also be conferred to a specific position by mutagenesis at another residue position (e.g. to displace a target residue).

Two aspects should be considered regarding alteration of a residue: 1) which of the 20 amino acids occupies that position (e.g. properties the specific amino acid contributes to the molecule at that position), and 2) the position of the specific amino acid within the protein (e.g. how position affects the amino acid's contributions to function). One way of altering a residue is by substituting a different amino acid at that position within the polypeptide chain. Alternatively, the positional location of a specific amino acid within the polypeptide chain can be displaced. This can be accomplished by inserting or deleting another residue, either nearby or via a long range structural mutation. Also, the specific residue can be deleted from the polypeptide chain without replacement by another amino acid. Any number or combination of these alterations can be used to produce a desired binding property of the mutant produced.

Since the structural data obtained from adenovirus serotype 12 is readily applicable to other adenoviruses (e.g. different serotypes and/or adenoviruses with other mutations) which bind CAR-D1 this method is applicable to any adenovirus serotype which binds CAR-D1. A residue(s) of the adenovirus fiber protein knob domain which is predicted to alter the binding properties of knob when mutated is first identified from the crystal structure coordinates of the Ad12knob:CAR-D1 complex, and when necessary the analogous residue(s) is identified through examination of amino acid homology of relevant adenovirus serotypes. The mutation(s) is then introduced into the genome of the adenovirus by standard methods.

Once the desired mutation(s) is introduced, the encoded mutant virus is produced and the CAR binding properties of the mutant virus are analyzed (e.g. by comparison with wild type) to verify that the mutant produced exhibits altered adenovirus-CAR binding properties. This analysis is accomplished by performing any number of standard binding assays known in the art. An altered binding property includes either a reduction or elevation in CAR-D1 binding affinity. Often, the objective will be to produce a mutant which has a reduction in CAR-D1 binding affinity. In one embodiment, the mutant generated has significantly weakened binding affinity for CAR-D1 relative to wild type adenovirus under physiological conditions. In addition, the binding specificity can also be altered, for example to produce a mutant adenovirus which binds a different molecule, such as a CAR mutant or a receptor other than CAR. In one embodiment, the receptor for which the mutant adenovirus binds is an engineered receptor.

Once residues or regions of knob are identified for mutagenesis, a random mutagenesis approach may be undertaken, followed by screening the mutant virions generated for the desired binding property. Alternatively, a more rational approach to designing a specific mutant may be undertaken by systematically introducing specific mutations calculated to produce the desired binding property alteration. The Exemplification below lists several Ad12 binding mutants produced by alteration of specific residues in knob identified on the basis of their structural location.

The present invention also provides a method for identifying an inhibitor of adenovirus binding to CAR through rational drug design. The method entails providing a three-dimensional structure derived by X-ray diffraction from a crystal of the adenovirus knob trimer bound to CAR-D1, and employing the three-dimensional structure to design or select a potential inhibitor. Once identified, the potential inhibitor is synthesized, and then tested for the ability to inhibit adenovirus binding to CAR. A positive result indicates that the potential inhibitor is an actual inhibitor. In a preferred embodiment, the crystal of adenovirus knob trimer bound to CAR-D1 has $P4_332$ space group symmetry with a cubic unit cell with 167.85 angstroms per side. The term "space group" refers to the arrangement of symmetry elements of a crystal. The term "unit cell" refers to the basic parallelepiped shaped block. The entire volume of a crystal may be constructed by regular assembly of such blocks. In a preferred embodiment, the atomic coordinates of the Ad12knob:CAR-D1 complex are obtained by means of computational analysis of X-ray diffraction data. The three-dimensional structure provided by Applicants is defined by atomic coordinates listed in the Protein Data Base under code 1KAC, and is well suited for use in this method.

A potential inhibitor may function by one of several different putative mechanisms. Without limitation, the inhibitor may function as a competitive inhibitor, a non-competitive or an uncompetitive inhibitor. A competitive inhibitor is one that inhibits activity by directly competing with the receptor or virus for the binding site. Competitive inhibition can be reversed completely by increasing the virus concentration. An uncompetitive inhibitor is one that inhibits by binding to the virus or receptor which is in complex. Uncompetitive inhibition cannot be reversed completely by increasing virus concentration. A non-competitive inhibitor can bind to either free or bound virus or CAR.

An inhibitor may be designed or selected to interact with a particular component or specific residues of a target molecule(s) to block binding. The target molecule(s) may be either the adenovirus fiber knob protein domain or the D1 domain of the CAR receptor, or both. The type of interaction between the inhibitor and the target molecule(s) may be any form or combination of interactions known in the art (e.g. covalent or non-covalent, especially hydrogen bonding,.hydrophobic, van der Waals, electrostatic). Also, the inhibitor compound must be able to assume a conformation which allows it to associate with the target molecule(s). Such conformational requirements include the overall three-dimensional structure and orientation of the chemical entity or compound in relation to all or a portion of the binding site or the spacing between functional groups of the inhibitor compound comprising several chemical entities that directly interact with the target molecule(s).

An inhibitor molecule may be computationally evaluated and designed by means of a series of steps in which chemical entities or fragments are screened and selected for their ability to associate with the individual binding pockets or other areas of the target molecule(s). The structure coordinates of the present invention may also be used to screen computationally small molecule databases for compounds that bind to one of more of the complex components.

Potential residues of knob to be targeted for interaction with an inhibitor include, without limitation, residues corresponding to D415, P417, P418, I426, V450, K451, Q487, Q494, S497 and V498 in one monomer of the Ad12 knob trimer, and P517, P519, N520, and E523 of the adjacent monomer of the Ad12 knob trimer and homologous residues in other CAR-D1-binding adenovirus serotypes. Preferably the interaction is non-covalent. Potential residues of CAR-D1 to be targeted for inhibitor interaction include, without limitation, P33, D37, L39, V48, D49, V51, L54, S56, Y61, E62, E63, Y64, K102, K104, A106 and P107 of human CAR-D1. Preferably, the interaction is non-covalent.

In another embodiment, the potential inhibitor is designed to interact, preferably non-covalently, with residues of knob and/or D1 which line one of the two cavities which are formed during adenovirus/CAR-D1 binding. Such residues are ideal candidates for interaction with a potential inhibitor, to block or disrupt virus-receptor binding. Small molecules which specifically fit into these cavities during binding and destabilize virus binding can be designed from the information provided regarding the topological mismatches of the interfacial components of D1 and knob. For instance, a small molecule designed to bind to residues lining a cavity of one component of the complex, but to repel residues lining a cavity of the other component of the complex would inhibit or disrupt complex formation and subsequently virus binding.

Potential inhibitors may be designed or assembled by a variety of methods known in the art. For instance, a potential inhibitor may be designed de novo, or alternatively may be designed from a known molecule (e.g. a known inhibitor). Once suitable chemical entities or fragments have been selected, they can be assembled into a single inhibitor compound. Assembly may proceed by visual inspection of the relationship of the fragments to each other on the three-dimensional image displayed on a computer screen in relation to the structure coordinates of the present invention. This would be followed by manual model building using software such as Quanta or Sybyl. Useful programs to aid one of skill in the art in connecting the individual chemical entities or fragments include:

1. CAVEAT (Bartlett et al., "CAVEAT: A Program to Facilitate the Structure-Derived Design of biologically Active Molecules". In "Molecular Recognition in Chemical and Biological Problems", Special Pub., Royal Chem. Soc., 78, p. 182–196 (1989)). CAVEAT is available from the University of California, Berkeley, Calif.

2. 3D Database systems such as MACCS-3D (MDL Information Systems, San Leandro, Calif.) reviewed in Martin, Y. C., "3D Database searching in Drug Design", J. Med. Chem., 35, p. 2145–2154 (1992).

3. HOOK, available from Molecular Simulations, Burlington, Mass.

In addition, inhibitory or other binding compounds may be designed as a whole or de novo using an empty binding site or optionally including portions of a known inhibitor(s). These methods include:

1. LUDI (Bohm, H. J., J. Comp. Aid. Molec. Design 6: 61–78 (1992)). LUDI si available from Biosym Technologies, San Diego, Calif.

2. LEGEND (Nishibata and Itai, Tetrahedron 47: 8985 (1991)). LEGEND is available from Molecular Simulations, Burlington, Mass.

3. LeapFrog, available from Tripos Associates, St. Louis, Mo.

Without limitation, other molecule modeling techniques which may also be employed in accordance with this invention are described by Cohen et al., *J. Med. Chem.* 33: 883–894 (1990), and Navia et al., *Current Opinions in Structural Bio.* 2: 202–210 (1992).

EXEMPLIFICATION

Section I: Expression and Characterization of CAR Extracellular Fragments

Expression and Purification of CAR Extracellular Fragments

To localize the Ad-binding activity of CAR, fragments corresponding the amino-terminal CAR IgV domain (D1) and the combined IgV+IgC2 domains (D1/D2) were expressed in *E. coli*. A cDNA fragment coding for D1 (FIG. 1b) was cloned into pET20b, an expression vector designed to export expressed proteins into the *E. coli* periplasmic space (FIG. 1c), but synthesis of D1 (expected molecular weight of about 16 kDa) was undetectable after 3 hours of induction. No bands corresponding to D1 were detected by SDS-PAGE analysis of whole cell lysates. When the initial construct was enlarged to include the downstream IgC2 domain (FIG. 1b), however, the resulting D1/D2 polypeptide was overexpressed and ran as a closely-spaced doublet on SDS-PAGE, which is characteristic of some periplasmic proteins such as alkaline phosphatase and results from partial hydrolysis of the signal peptide. These results imply that the amino-terminal domain (D1) specified by the initial construct also entered the secretory pathway, but probably was rapidly degraded in the periplasmic space. The D1/D2 protein fragment was not soluble in *E. coli* cells grown at temperatures ranging from 18–37° C.

To determine if D1 could be stabilized by restricting its synthesis to the cytoplasm, the D1-encoding PCR product was transferred as a NcoI-XhoI restriction fragment from pET20b into pET15b (FIG. 1c). Because of restriction site differences between these 2 expression vectors, the CAR protein fragment specified by this construct (pET15b-sD1) had a vector-encoded 22-amino acid carboxy-terminal extension (SEQ ID NO: 1) and it lacked the amino-terminal hexahistidine tag that is normally attached to proteins expressed from pET15b (FIG. 1c). The resulting polypeptide was expressed at moderate abundance at 37° C., but was insoluble. When the cultures were induced at 18° C., however, a significant amount of D1 was contained in the soluble fraction of cell lysates. SDS-PAGE of the lysate and fractions revealed a band corresponding to the 16 kDa molecular weight of D1 present in all fractions. The larger CAR cDNA fragment encoding D1/D2 also was transferred from pET20b into pET15b, but none of the expressed protein was detected in the soluble fraction of cell lysates. SDS-PAGE analysis of cell lysate and fractions revealed bands corresponding to the molecular weight of about 27 kDa in both the whole cell lysate and insoluble fraction, but absent in the soluble fraction. Soluble D1 (sD1) was partially purified by ammonium sulfate precipitation and ion-exchange chromatography.

To determine if removal of the vector-encoded carboxy-terminal extension would increase the yields of soluble CAR fragments produced in *E. coli*, cDNA fragments encoding D1 and D1/D2 were amplified with new primer sets (primers 6–8, FIG. 1b) that introduced downstream stop codons and also fused the proteins to the vector-encoded amino-terminal hexahistidine tag. Both CAR fragments were overexpressed, but were insoluble at culture growth temperatures between 18–37° C., suggesting that the carboxy-terminal extension specified by the initial pET15b-sD1 construct may enable the IgV domain to fold into a soluble structure within *E. coli* cells. The insoluble his-tagged CAR fragments were both refolded from urea-solubilized inclusion bodies and were purified to apparent homogeneity by anion exchange chromatography. To confirm that D1 solubility within intact *E. coli* cells depends on the presence of the 22 amino acid C-terminal extension rather than the absence of the N-terminal hexahistidine leader, the D1-encoding insert (PCR product of primers #6 and #7, FIG. 1b) was transferred from pET15b into pET11a as an NdeI-BamHI fragment (FIG. 1c). D1 was overexpressed in pET11a-D1-transformed cells, but was completely insoluble, as determined by comparison of whole cell lysate to soluble cell fractions by SDS-PAGE analysis, confirming that the C-terminal 22 amino acid extension specified by pET15b increases D1 solubility.

Biological Activity of CAR Extracellular Fragments

Refolded D1 and D1/D2 CAR fragments were examined for the ability to form specific complexes with recombinant fiber knob from Ad12. It was previously reported that infection of HeLa cells by Ad12 virus is inhibited by purified native fiber protein from Ad2, suggesting that CAR serves as the major attachment receptor for both Ad2 and Ad12. Because Adenovirus type 5 and type 2 are members of the same subgroup (C) of adenovirus, it is expected that CAR is also the major attachment receptor for Ad5. A fragment of Ad12 DNA coding for the fiber knob domain (FIG. 1a) was cloned in pET15b. Ad12 knob was abundantly expressed following IPTG induction of cultures at 37° C., but accumulated entirely within the insoluble fraction of cell lysates. When cultures were induced at 24° C., however, the majority of knob was in the soluble fraction. The knob was purified by ammonium sulfate precipitation and anion exchange chromatography, and the his-tag was removed by digestion with thrombin. A sample of purified Ad12 knob, visualized by SDS-PAGE, displayed as a single band at the expected molecular weight. Ad12 knob was then incubated with the his-tagged D1 or D1/D2 in the presence of purified Ad2 hexon protein (included as a specificity control). The mixtures were then adsorbed to Ni-NTA beads to capture the his-tagged CAR fragments. In control incubations lacking the CAR fragments, Ad12 knob and Ad2 hexon both failed to bind to Ni-NTA beads, demonstrated by an absence of bands upon SDS-PAGE analysis of bead eluate. In the presence of either D1 or D1/D2, however, Ad12 knob bound to Ni-NTA beads and could be easily detected in bead eluate by SDS-PAGE analysis, whereas Ad2 hexon did not. This suggested that the CAR IgV domain (D1) specifically binds the Ad12 knob. This conclusion was supported by the results of an experiment to test whether his-tagged Ad12 knob and sD1 form specific complexes. Purified, his-tagged Ad12 knob was mixed with a partially purified preparation of sD1 and incubated briefly to allow protein complexes to form. The mixture was then applied to a column of Ni-NTA beads, unbound proteins were washed from the column, and the bound fraction was eluted with EDTA. SDS-PAGE analysis of the bead eluate revealed the presence of Ad12 knob and sD1, seen as two distinct bands at their expected molecular weights. Thus, D1 alone is sufficient for binding to the Ad12 knob.

To determine if the binding activities of the recombinant Ad12 knob and the CAR IgV domain have the same specificities as their native fiber and CAR counterparts, the ability of Ad12 knob and sD1 to inhibit Ad2 infection of HeLa cells was tested. As shown in FIG. 2, Ad2 infectivity was significantly inhibited when either sD1 or Ad12 knob was included in the virus inoculum during virus adsorption. No inhibition of infection was observed in cell cultures that were pretreated with sD1 and then washed prior to virus adsorption, indicating that the inhibitory activity of sD1 does not result from a cytotoxic effect on cells. Cells similarly pretreated with Ad12 knob, however, remained significantly refractory to infection by Ad2 virus. This most likely results from incomplete dissociation of knob from the CAR receptors on cells rather than a cytotoxic effect. Thus, the binding specificity of native fiber and CAR is reconstituted in recombinant Ad12 knob and sD1. These results further substantiate that CAR serves as the major attachment receptor for Ad2 (and Ad5).

Physical Characteristics of Ad12 Knob and CAR Domains

Figure 3:
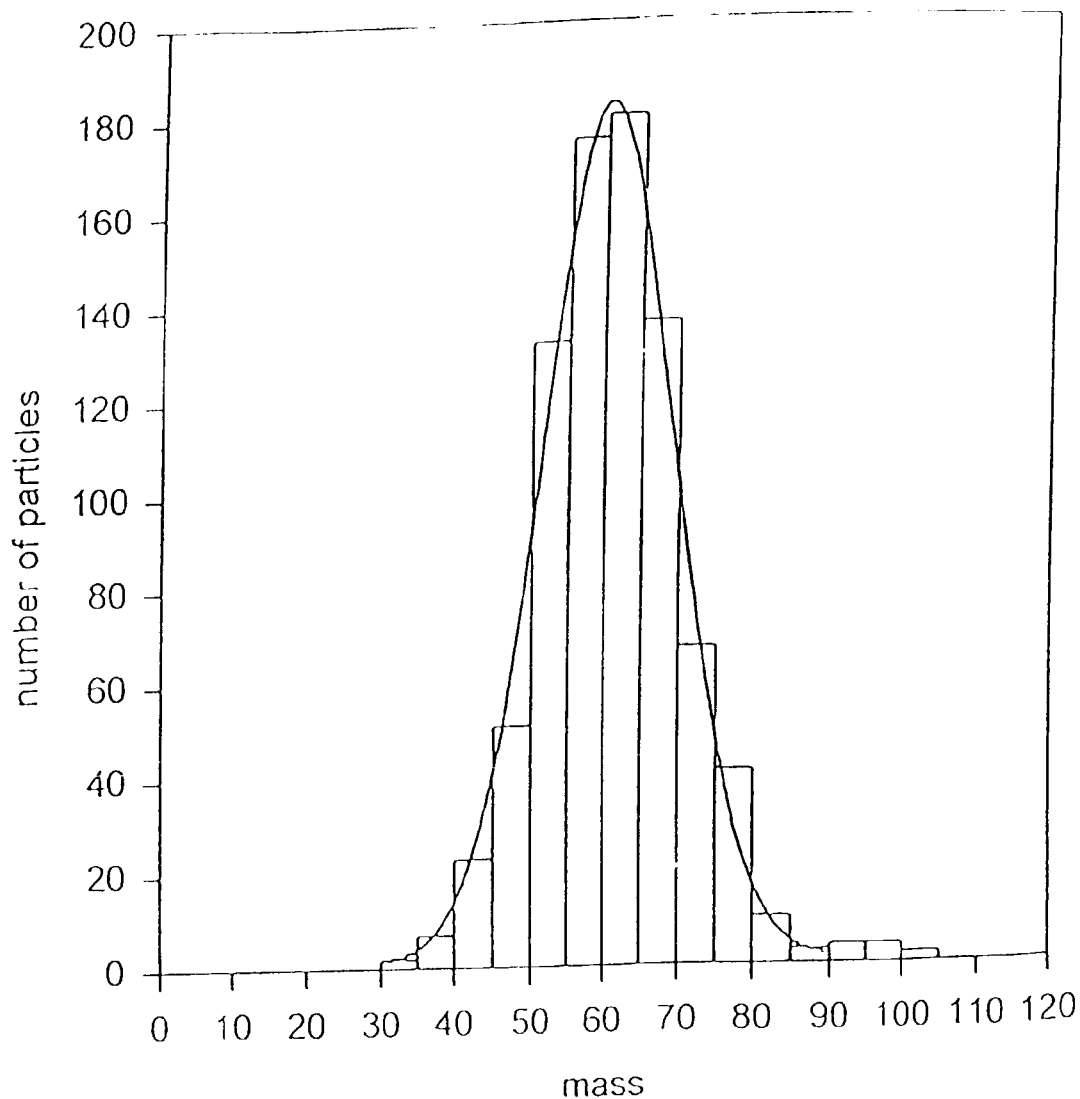
FIG. 3 is a diagrammatic representation of data from scanning transmission electron microscopy (STEM) analysis experiments measuring the mass of Ad12 knob.

Analysis of boiled and untreated samples of Ad12 knob by SDS PAGE showed bands of 20 and 60 kDa, respectively, suggesting that, like the Ad5 fiber knob, the Ad12 knob is trimeric. To confirm this result, a sample of Ad12 knob was examined in the Brookhaven scanning transmission electron microscope (STEM), which measures the mass/unit length of macromolecules. In good agreement with the PAGE results, STEM analysis showed the Ad12 knob has a mass of 60.6 kDa (FIG. 3).

Figure 4:
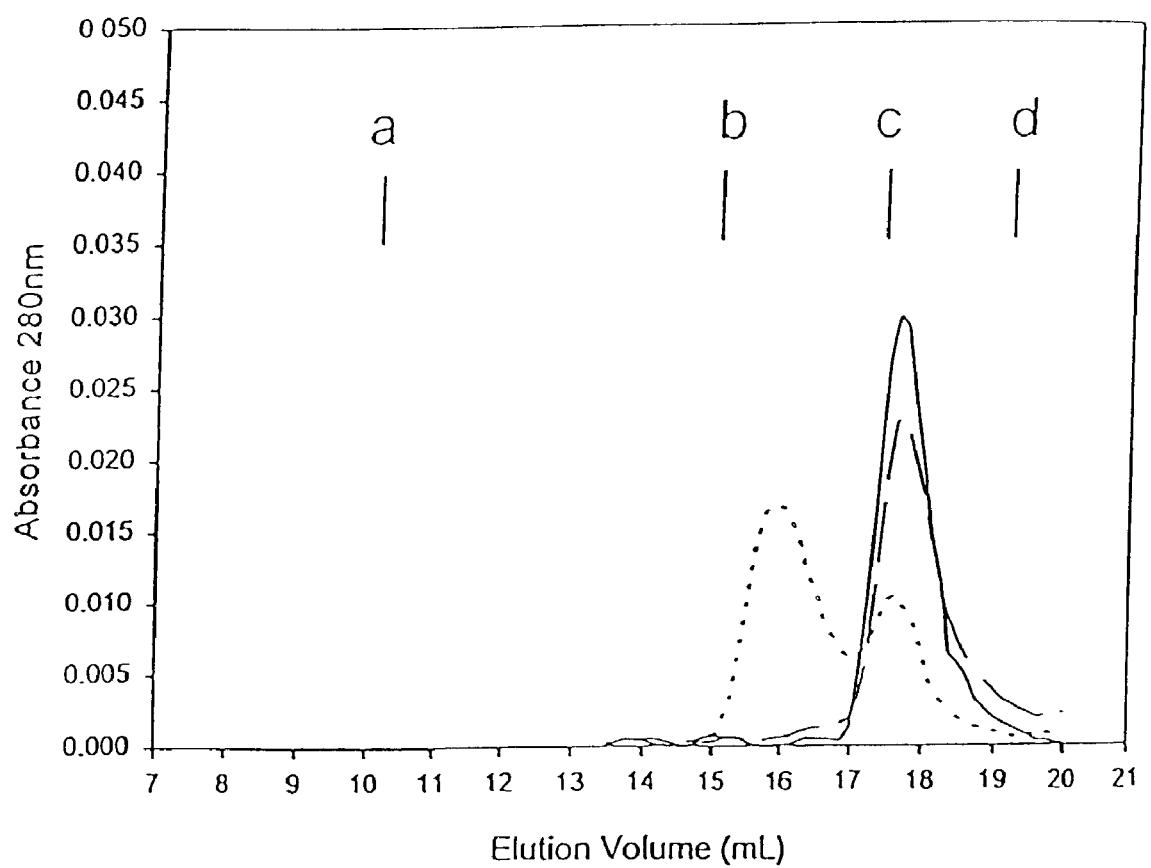
FIG. 4 is a diagrammatic representation of data from size exclusion chromatography of knob, CAR domains and knob-CAR complex. 20 µL aliquots of purified 41.7 µM CAR D1/D2 (-), 40.7 µM Ad12 knob (- - -), or a mixture containing 32.4 µM knob and 30 µM D1/D2 (. . . .) were chromatographed on a Superose 6 gel filtration column at a flow rate of 0.25 mL/min (all of the concentrations given refer to the monomeric species). The marks show the elution position of size markers: a, earthworm hemoglobin (3.8 MDa); b, dodecameric earthworm hemoglobin (200 kDa); c, bovine serum albumin (67 kDa); and d, cytochrome c (12 kDa).

The Ad12 knob and the refolded D1 and D1/D2 CAR domains were subjected to gel filtration chromatography to determine their native sizes (FIG. 4). In all three cases, the proteins eluted as symmetric peaks in an elution volume that was independent of the protein concentration (1–500 µM monomer). D1 consistently eluted as a ~30 kDa species while both D1/D2 and knob eluted as ~60 kDa species. Based upon the primary amino acid sequences of these proteins, the gel filtration data suggest that both D1 and D1/D2 are dimers while Ad-12 knob is a trimer. When D1/D2 and knob were mixed together at equimolar (monomer:monomer) ratios two peaks were observed in the elution profiles, a low molecular weight species eluting at a position corresponding to free Ad12 knob or D1/D2 and a higher molecular weight species eluting at a molecular mass of ~100 kDa. Fractions from the two peaks were analyzed by SDS-PAGE, which revealed that the high molecular weight peak corresponded to the knob-D1/D2 complex, while the lower molecular weight species was free D1/D2. Similar results were observed for complexes of knob and D1, which eluted at ~80 kDa.

Methods of the Invention: Section I

Expression and purification of Ad12 knob. A DNA fragment encoding the entire Ad12 fiber knob domain and several flanking amino acids from the fiber shaft (amino acids 401–587) (corresponding to nucleotides 30571–31128 of GenBank Accession #X73487) was amplified from viral DNA by PCR (30 cycles of 94° C./30 sec, 55° C./40 sec, 72° C./60 sec) using primers #1, CATATGAGCAACACTC-CATACG (SEQ ID NO: 2), and #2, GGATCCTTATTCT-TGGGTAATGT (SEQ ID NO: 3), (FIG. 1a). The resulting PCR product was cloned between the NdeI and BamHI sites of pET15b (Novagen) and transformed into strain BL21-DE3 (Novagen) for protein expression. Overnight cultures grown in LB broth containing 150 mg/L penicillin G (Sigma) were diluted 100-fold into fresh LB-penicillin broth and grown at 37° C. until midlog phase (OD of 0.8 at 600 nm) at which time they were chilled to 24° C. and adjusted to 50 µM IPTG (isopropyl β-D thiogalactopyranoside) to induce knob expression. After shaking (250 rpm) overnight at 24° C., the cells were collected by centrifugation, resuspended in 10% of the original culture volume of STE (10 mM Tris-HCl pH 8.0, 100 mM NaCl, 1 mM EDTA (ethylenediaminetetraacetic acid)) containing 100 µg/ml lysozyme, and subjected to 3 cycles of freezing and thawing. The viscous cell lysate was then sonicated and cleared by centrifugation at 25,000×g for 10 min. Knob was precipitated from the supernatant by addition of solid ammonium sulfate to 35% saturation (25° C.), dialyzed against several changes of 10 mM Tris-HCl (pH 7.5) and passed over a column of DEAE-cellulose (DE52, Whatman) equilibrated in the same buffer. Knob was recovered from the flow-through fractions essentially free of contaminating E. coli proteins and nucleic acids, and was further purified by Ni-NTA affinity chromatography according to the manufacturer's instructions (Qiagen). About 100 mg of purified Ad12 knob was obtained from one liter of bacterial culture.

Expression and purification of CAR protein fragments. cDNA fragments encoding the human CAR extracellular domains (D1 and D1/D2, FIG. 1b) were amplified by RT-PCR of total RNA from a mouse A9 cell line transformed with multiple copies of the cloned human CAR gene. First strand cDNA synthesis was primed by oligo-dT. Primers #3: CCATGGGTATCACTACTCCTGAAGAGA (SEQ ID NO: 4) (the first 6 nucleotides add two upstream codons, encoding M20 and G21. The remaining nucleotides correspond to nucleotides 121–141 of GenBank Accession #Y07593), #4: CTCGAGCGCACCTGAAGGCTTA (SEQ ID NO: 5) (complementary to GenBank Accession #Y07593 nucleotides 476–491) #5: CTCGAGTGAAGGAGGGACAAC (SEQ ID NO: 6) (complementary to GenBank Accession #Y07593 nucleotides 744–758) (FIG. 1b) were designed for cloning D1- and D1/D2-encoding PCR products between the NcoI and XhoI sites of expression vector pET20b (Novagen). The PCR cycling program was identical to that used for Ad12 knob. These same PCR products were also cloned into pET15b as NcoI-XhoI restriction fragments, and thus lacked the vector-encoded hexahistidine tag, and each had an additional 22 amino acid-long carboxy-terminal extension encoded by vector sequences downstream of the XhoI site (FIG. 1c). Another set of primers (#6–#8, FIG. 1b) was designed to adapt the CAR PCR products for cloning between the pET15b NdeI and BamHI restriction sites, which provides for attachment of the amino-terminal hexahistidine tag to the expressed proteins. Primer #6: CATATGGGTATCACTACTC (SEQ ID NO: 7)(the first 7 nucleotides add two upstream codons, encoding M20 and G21. The remaining nucleotides correspond to nucleotides 121–132 of GenBank Accession #Y07593), #7: GGATC-CTACGCACCTGAAGGCT (SEQ ID NO: 8) (complementary to nucleotides 478–493 of GenBank Accession #Y07593) and #8: GGATCCTATCCAGCTTTATTTGAAG (SEQ ID NO: 9)(complementary to nucleotides 754–770 of GenBank Accession #Y07593). Stop codons were built into the reverse primers to avoid synthesis of the CAR fragments with the vector-encoded carboxy-terminal extensions.

The procedure used for expression of the initial pET15b-D1 construct (PCR product from primers #3 and #4) was similar to that described above for Ad12 knob except that the culture was induced at 18° C. Soluble D1 (sD1), produced from the pET15b NcoI/XhoI construct, was precipitated from cleared cell lysates by ammonium sulfate precipitation (35–60% cut, 25° C.) and was partially purified by anion exchange chromatography (DE52) in 10 mM Tris-HCl buffer (pH 7.5). About 5 mg of partially purified sD1 was recovered from one liter of bacterial culture. The hexahistidine-tagged CAR fragments expressed from the second set of pET15b constructs (using primers #6–#8, FIG. 1b) were insoluble, but were recovered from inclusion bodies. Cultures were induced at 37° C., and cleared lysates were prepared as described above. After centrifugation, the supernatant was discarded, the pellet was washed several times in STE containing 0.1% NP40, dissolved in 8 M urea/50 mM β-mercaptoethanol/50 mM Tris-HCl (pH 9.2) (20 ml per liter of initial culture), and then diluted with 15 volumes of 20 mM Tris-HCl (pH 8.0). The slightly hazy solution was passed through a 10 ml bed volume of DEAE-Sepharose Fast Flow (Pharmacia) equilibrated in 20 mM Tris-HCl (pH 8.0). Approximately half of the bound CAR fragments eluted with 50 mM NaCl and were essentially pure. The remaining bound CAR eluted with 300 mM NaCl along with contaminating E. coli proteins, and was discarded.

Export of CAR D1 and D1/D2 into the E. coli periplasm. Mid-log phase cultures of strain BL21-DE3 cells transformed with pET20b-D1 and pET20b-D1/D2 were treated with IPTG to induce synthesis of D1 and D1/D2. After 3 hr of induction, whole cell lysates were prepared and analyzed by SDS-PAGE.

D1 and D1/D2 expression and solubility in the E. coli cytoplasm. BL21-DE3 cells transformed with pET15b-D1 and pET15b-D1/D2 (PCR products from reactions with primers 3–5, FIG. 1b) were induced with IPTG at 18° C. Protein content of whole cell lysates and of the soluble and insoluble fractions of cell sonicates were analyzed by SDS-PAGE.

Assays for detection of knob-CAR complexes. The hexahistidine tag was cleaved from Ad12 knob using biotinylated thrombin and was then passed through Ni-NTA and avidin columns to remove residual his-tagged proteins and thrombin. The resulting knob was mixed with purified Ad2 hexon protein and then divided into 3 equal samples. His-tagged D1 or D1/D2 were then added to 2 of the samples, and an equivalent volume of buffer added to the third (control) sample. Each sample was then batch-adsorbed to Ni-NTA beads, washed, and eluted with 100 mM EDTA/25 mM Tris-HCl (pH 8.0). Samples were then electrophoresed in SDS-polyacrylamide gels and stained with coomassie blue.

Inhibition of Ad2 infection of HeLa cells. HeLa monolayer cultures were grown in 50% Dulbecco's modified Eagle medium (DMEM, Gibco)/50% Ham's F12 Nutrient Mixture (Gibco) containing 10% calf serum. Monolayers were seeded in 24-well cluster plates 1 day before infection. Ad2 virus diluted in binding buffer (50% DMEM, 50% PBS, 0.4% bovine serum albumin) was divided into 3 equal samples and mixed with an equal volume of Ad12 knob, sD1 (both approximately 2 mg/ml in PBS) or an equal volume of binding buffer. Each preparation was adsorbed in triplicate (0.2 ml/well) for 30 min at 4° C., the wells were then washed twice with PBS and incubated for 2 days at 37° C. in DMEM containing 2% calf serum. The number of infected cells in each culture was then determined by immunoassay for the viral hexon antigen as previously described (Bai et al., J. Virol. 67: 5198–5205 (1993)). To control for possible cytotoxic effects of the recombinant proteins, additional sets of cultures were preincubated with Ad12 knob or sD1 (1 mg/ml) in binding buffer for 30 min, washed twice with PBS and then infected with Ad2 virus.

Analysis of Ad12 knob by scanning transmission electron microscopy (STEM). The mass of Ad12 knob (with the His tag removed) was measured by STEM. Five microliters of the purified protein (~10 mg/ml) was applied to an electron microscope holey grid covered with thin (~2 nm) carbon, and after 1 minute was wicked and washed 10 times with 20 mM ammonium acetate. The grid was blotted and rapidly frozen in liquid nitrogen slush, then freeze-dried overnight. Data was collected with the Brookhaven NIH Biotechnology Resource STEM (Wall, J. S. (1982) in Introduction to Analytical Electron Microscopy, Plenum, N.Y., p 333–342) at scans of 0.512 micron width with a dose of 200 electrons/$nm^2$. Protein particle masses were measured (Wall et al., Annu. Rev. Biophys. Biophys. Chem. 15: 355 (1986)) off-line using the "PC-Mass" program, and statistics and curve fitting were generated with SigmaPlot. Mass calibration was done using TMV particles adhered to the grid before the sample was applied.

Gel filtration analysis of Ad12 knob and CAR D1 and D1/D2. The native molecular masses of Ad12 knob, the refolded D1 and D1/D2 domains of CAR, and knob complexed to D1 or D1/D2 were determined by size exclusion chromatography using a Superose 6 gel permeation column. In brief, 20 □L aliquots of purified proteins or protein complexes were chromatographed at 0.25 ml/min on the Superose 6 column in 20 mM TrisHCl pH 7.8, 200 mM NaCl, 1 mM DTT and 0.1 mM EDTA. Aliquots of the fractions were analyzed by SDS-PAGE. These experiments were run over a range of concentrations from 1–500 μM monomer.

Section II: Crystal Structure of Adenovirus Fiber Knob Domain and CAR-D1

The structure of Ad serotype 12 (Ad12) fiber knob domain (knob) (fiber protein residues 401–587) alone, is reported here and in Bewley, et al. Science 286:1579–1583 (1999), the contents of which are incorporated herein by reference, at 2.6 Å resolution (Table 1). The structure is essentially identical to that of the previously determined Ad serotype 5 (Ad5) knob (RMS deviation on equivalent C positions=0.8 Å) (Xia et al., Structure 2: 1259–70 (1994)). Knob monomers adopt an eight-stranded antiparallel β-sandwich fold with strands J, C, B, and A comprising the so-called V-sheet that provides the majority of contacts in the tightly packed trimer interface, and strands G, H, D and I form the solvent exposed R-sheet. Although the structure of Ad12 knob is essentially identical to that determined for the Ad5 knob, the one notable difference between the structures of the Ad5 and Ad12 knobs is in the HI loop. In Ad12 the HI loop in Ad12 (residues 548–556) is well ordered whereas in Ad5 the HI loop (residues 536–549) is five residues longer and is disordered (Xia, et al., 1994).

The location of the CAR binding site on Ad12 knob was determined experimentally by solving the structure of the Ad12 knob CAR-D1 complex (Table 1) and Bewley et al. (1999). In this complex, CAR-D1 (preCAR residues 22–144)) has an Igv-like β-sandwich fold, and binds at the interface between two adjacent Ad12 knob monomers producing a triskelion shaped complex without any significant rearrangement in the knob structure. The complex is formed by the AB loop, the carboxyl ends of the DE loop, and the very short F strand of one knob monomer and the FG loop of an adjacent knob monomer interacting with a single face of the CAR-D1 sandwich (strands C, C', C", and the second half of F). The amino-terminal end of the knob molecule, which is attached to the viral fiber shaft domain in vivo, is on the opposite face to the carboxyl terminus of CAR-D1. Although the current model does not provide direct information concerning the location of CAR-D2 (residues 126–222) comparisons of CAR-D1 with structures of homologous proteins, solved with both D1 and D2 domains (CD4:1cdh.pdb, ICAM-1:1iam.pdb & 1icl.pdb, and ICAM2:1zxq.pdb, where the names of the molecules are followed by their Protein Data Bank access identification numbers), suggest that CAR-D2 will not make extensive contacts with knob. This observation is consistent with the biochemical data presented in Section I above, indicating that D1 alone is necessary and sufficient for knob binding. The high efficiency of Adenovirus infection may be due, in part, to the three CAR binding sites on each fiber knob. Thus, each virion contains 36 high-affinity CAR binding sites ensuring that most collisions with the cell surface will result in viral attachment, while at least 12 and possibly as many as 36 antibodies are required for neutralization of all the CAR binding sites on each virion.

Based on the crystal structure of the Ad5 knob Xia et al. (*Structure* 2: 1259–70 (1994)) had proposed two putative CAR binding sites, the first at the trimer interface and the second on the surface of each of the R-sheets. To examine the hypothesis concerning interactions of the R-sheets, a set of single site amino acid substitutions in the R-sheet were made. The substitutions did not abrogate CAR-D1 binding (see Table 2) and only one of the set resulted in a slight reduction in CAR-D1 binding (L430A), results which argue against the involvement of R-sheet amino acids in the interaction with CAR-D1.

The knob-CAR-binding site proposed here is strongly supported by mutational analysis (see Table 2). Specific mutations in the AB loop significantly diminished or completely abrogated CAR-D1 binding. Because of sequence conservation in the AB loop among the CAR-D1-binding subgroups of adenovirus (Table 3), homologous mutations in the AB loop of such CAR-D1-binding adenovirus genomes are predicted to result in a similar reduction in CAR-D1 binding by the resulting mutant adenovirus. This is particularly the case for sub-group C adenoviruses represented by serotypes Ad2 and Ad5.

The loss of CAR-D1 binding activity in the HI loop mutant (Table 2, ΔG550/I551) is thought to result from loss of water-mediated hydrogen bonds between the N and O of G550 in the HI loop and the O of R518 and N of A521 in the FG loop which normally stabilize the FG loop in a conformation where it can make direct contacts with CAR-D1. Because of the additional five amino acids in the HI loops of Ad 2 and Ad5 it is possible that more extensive deletions of the Ad2 and Ad5 HI loop amino acids would be required to have a similar effect on the binding of CAR-D1 by Ad5 or Ad2. For example, a deletion of up to seven amino acids would create Ad5 and Ad2 mutants that are homologous to the ΔG550/I551 Ad12 mutant of Table 2.

The results presented here also indicate that relying on mutational analysis in the absence of a structure to identify the receptor binding sites on knob can prove misleading, because most of the trimeric knob surface which is accessible to receptors is composed of loops whose conformations may be altered by long range effects.

In the Ad12 knob trimer and all other CAR-binding serotypes, there are two sets of solvent exposed regions whose sequences are conserved. The first is located on the virion-facing surface where the shaft domain begins and the second is located at the side of the molecule on a ridge between adjacent monomers. This ridge is comprised primarily of residues from the relatively conserved AB loop that becomes buried in the complex. In total, complex formation buries 1880 Å$^2$ of mixed hydrophobic and hydrophilic surfaces at each knob-CAR interface, 970 Å$^2$ contributed from knob and 910 Å$^2$ from CAR-D1. The majority of the buried surface in knob is contributed by one monomer (770 Å$^2$) with the second making a relatively small contribution (200 Å$^2$). The actual surface area involved in protein-protein contacts across this interface is ~15% smaller due to a mismatch in their surface topology. The contact residues in each molecule draw out a serpentine which, when united with its partner, create two adjacent cavities, discussed below.

Fourteen residues in knob and sixteen residues in CAR-D1 make direct interactions across the interface including 7 hydrogen bonds. The AB loop of knob is a key anchor, contributing over 50% of interfacial interactions, including the three hydrogen bonds between conserved residues (D415O/K104Nζ, L426O/Y64OH, and K429Nζ/E37Oε2of knob/CAR-D1, respectively). The AB loop spans the width of the CAR-D1, held at one end by D406 of knob and at the other end by E416 of knob, which changes rotomer conformation upon CAR-D1 binding to accommodate the approaching side chain of Y61. In the middle of the AB loop, the conserved residue P418 of knob makes contacts with residues E37, V51 & L54 in CAR-D1. The importance of this loop is emphasized when comparing the sequence of non-CAR binding Ad serotypes such as subgroup B (serotypes 3 and 7), which have evolved to bind a different receptor (Roelvink et al., *J Virol* 72: 7909–15 (1998)), or serotypes 40 and 41 where two types of fiber exist on the same virus, only one fiber type binds CAR (Yeh et al., *Virus Res* 33: 179–98 (1994)). The sequences of the AB-loop of knob in the non-CAR binding serotypes diverge widely from each other and from known CAR binding serotypes (Table 3). Specifically, the knob domains in non-CAR binding fibers have either insertions or deletions in the AB loop relative to the conserved residues, P418 & N419 of the CAR-D1-binding subgroups.

In order to further explore the idea that the AB loop is an important determinant in CAR binding, a number of knob variants that mimic non-CAR-binding knobs in this region were constructed. The double substitution P417E/P418A which converts the Ad12 AB loop to a sequence similar to Ad3, the insertion of TI between S421 and L422, which lengthens the AB loop and the deletion E425 & L426, which shortens the AB loop, all abrogated CAR-D1 binding (Table 2) Similarly, the substitution of Thr-Thr-Ala (TTA) for P417–P418 is predicted to abrogate CAR-D1 binding by Ad12 since the substitution would then lengthen the AB loop in addition to mimicking the AB loop of non-CAR-D1 binding Ad3. These mutants are consistent with the hypothesis that much of the selectivity of adenovirus serotypes for CAR involves interactions with the AB loop. Tt is likely that similar substitutions, insertions or deletions in other CAR-D1-binding adenovirus subgroups will have similar effects on CAR-D1-binding. For example, a double substitution such as S408E and P409A or substitution of S408 and P409 with the Thr-Thr-Ala (TTA) in Ad5 or Ad2 would be predicted to abrogate CAR-D1 binding by such mutants as would an insertion between R412 and L413 of Ad5 or between R412 and I413 of Ad2. Similarly, deletions which shorten the AB loop of Ad2 or are predicted to cause a similar reduction in CAR-D1 binding.

Topological mismatches over the AB loop and at other discrete regions of the interface result in the formation of two adjacent approximately equal-sized cavities totaling ~120 Å$^3$. They are separated by the interaction of P418 with residues in CAR-D1, pinching off communication between them. The cavities are lined with a mixture of hydrophobic and polar groups, more than 60% of which are either part of the backbone or are conserved in sequence. The two interfacial cavities are estimated to accommodate a total of ~4 water molecules, although in the current structural model only one well-ordered water molecule was observed. This water molecule forms a bridging interaction with the conserved/backbone atoms of E37Oε1, K102Nζ in CAR and D415O, P416O and K429Nζ in Ad12 knob. Weaker electron density was also observed throughout the two cavities, which may be indicative of additional mobile water molecules not sufficiently ordered at this resolution to be included in the current model.

Since the presence of such interfacial cavities in protein-protein complexes is atypical, it is striking that similar cavities exist at the interface between HIV gp120 and CD4 (Kwong et al., *Nature* 393: 648–659 (1998)), currently the only other virion-protein receptor complex whose structure has been determined by crystallography. In addition, the adhesion proteins of both viruses use surface loops to interact with the C-C'-C" face of respective receptors which both belong to the IgV superfamily. Moreover, in both complexes the viral proteins contribute approximately the same amount of surface area to the interface, burying a similar ratio of conserved and non-conserved residues.

These results, and those of others, now suggest that viruses have developed at least two structural means of evading immune attack. In picornoviruses, the receptor binding sites, including by extension the CAR binding site on coxsackievirus B, are associated with deep crevices or canyons on the capsid surface (Muckelbauer et al., *Structure* 3: 653–667 (1995)), which have been suggested to act as an antigenic shield for the conserved residues that define receptor binding specificity (Rossmann, M. G., *J.B.C.* 264: 14587–14590 (1989)). By contrast, the structures of the Ad12 knob-CAR-D1 and the HIV gp120-CD4 (Kwong et al., *Nature* 393: 648–659 (1998)) complexes show that solvent exposed loops comprise their receptor binding faces thus exposing them to immunoselective pressure. Water molecules that become trapped within interfacial cavities in both virus systems mediate specific bridging hydrogen bonds and van der Waals contacts across the interface. In contrast to direct amino acid contacts across the interface, which are very sensitive to changes in sequence, these indirect water-mediated contacts may be able to tolerate a higher degree of antigenic drift while still maintaining receptor-binding specificity.

The structure coordinates of the Ad12knob:CAR-D1 complex are deposited in the Protein Data bank (Abola et al., in Crystallographic Databases, Information Content, Software Systems, Scientific Applications (eds. Allen, F. H., Bergerhoff, G. & Sievers, R.) 107–132 (Data Commission of the International Union of Crystallography, Bonn/Cambridge/Chester, 1987) under access identification number 1KAC. The structure coordinates of isolated Ad12knob are deposited in the same database under access identification number 1NOB.

Methods of The Invention: Section II

Protein expression, purification and crystallization. The knob fiber protein (Ad12 knob) and the N-terminal fragment (residues 22–125) of the cellular receptor (CAR-D1) were expressed in *E. coli* and purified as described previously (Freimuth et al., *J. Virol.* 73: 1392–8 (1999)). Prior to crystallization, the purified proteins were proteolysed with 10 µg/ml trypsin, the 1:3 (trimeric knob: CAR-D1) complex formed and purified by anion exchange chromatography. Crystals of Ad12 knob were grown at room temperature using the sitting drop vapor diffusion method from a protein solution of 20 mg/ml suspended over a reservoir of 26% PEG3350. Showers of small poorly ordered crystals grew over the course of a week which were harvested, washed in 30% PEG3350 and seeded into a drop containing equal volumes of protein and 26% PEG3350 over a reservoir of 26% PEG3350. Large, rhombohedral plates grew overnight. They were transferred into a solution containing 50% PEG3350 and cooled directly into a stream of nitrogen at 99K. Crystals of the Ad12 knob/CAR-D1 complex were grown at room temperature using the sitting drop vapor diffusion method from a protein solution of 10–12 mg/ml and a reservoir of 0.9 M ammonium sulfate in 100 mM MES (pH 6.2). A typical crystal had a cubic habit and grew to 1.0 mm over a period of ~10 days. They were cooled directly into a stream of nitrogen at 99K, using 50% ethylene glycol as a cryoprotectant.

Structure Determination and refinement. The crystal structure of the knob-CAR-D1 complex was determined using crystals which had $P4_332$ space group symmetry. The unit cell was cubic (all sides of equal length) with 167.85 angstroms per side.

Each data set was collected from a single crystal at 99K using the NSLS beamlines X8C, X12C, and X25 at Brookhaven National Laboratory, Upton, N.Y. with either a Mar345 imaging plate detector, or the Brandeis 4-cell CCD detector. Mercury was introduced into Knob-CAR-D1 complex by soaking a single CAR-D1-knob complex crystal in 10 mM thimerosal for 6 hours. The data was collected on X12C using the Brandeis 4-cell CCD at a wavelength of 1.0 Å. In all cases, the crystals were cooled using an Oxford Cryostream. Raw data were reduced and scaled using the HKL program Suite (Otwinowski, Z. & Minor, W. in *Methods in Enzymology* (eds. Carter, C. W. & Sweet, R. M.) 307–326 (Academic Press, 1997)). All further calculations leading to the structure solutions were performed using programs in the CCP4 program Suite (CCP4. *The SRC(UK) Collaborative Computing Project No. 4: A Suite of Programs for Protein Crystallography.* (Daresbury, UK., 1991)).

The structure of Ad12 knob was solved by molecular replacement, using a monomer of Ad5 knob (1KNB.PDB) as a search model. The Ad12 knob is 48% identical and 78% similar in sequence to the Ad5 knob which also binds CAR (Bergelson et al., *Science* 275: 1320–3 (1997)). Two families of peaks were found in the cross rotation function, relating to two trimers. Based on an estimation of the Matthews coefficient (Matthews, B. W., *J. Mol. Biol.* 33: 491–497 (1968)) the asymmetric unit contained 1 or 2 trimers. The asymmetric unit contained six molecules based on the increasing correlation coefficient above the level of noise. Attempts to position of a seventh molecule reduced the correlation coefficient and we took this as evidence that the molecule contained 6 and not 3 monomers in the asymmetric unit. The structure was refined using the rigid body and simulated annealing protocols in CNS (Brunger et al., *Acta Crystallogr. D. Biol. Crystallogr.* 54: 905–21 (1998)) using tight NCS restraints, punctuated by rounds of model building. The current model contains residues 394–578 and 47 water molecules with good geometry (RMS deviation on bond lengths and bond angles is 0.009 Å and 1.6° respectively). It has an R-factor of 23.9% with a corresponding $R_{free}=29.4\%$.

The structure of Ad12 knob-CAR-D1 complex was determined using a combination of SIR, solvent flattening and molecular replacement. The refined structure of the Ad12 knob monomer described above was used as a search model in molecular replacement. A single clear solution was found corresponding to a single monomer in the asymmetric unit close to the crystallographic three fold axes. Positioned in this way, the biological trimer was generated by the crystallographic 3-fold of the unit cell. At this point, no interpretable density corresponding to the CAR-D1 molecule was visible, therefore, a thimerosal derivative data set was collected. The position of the mercury was identified in a difference map, calculated between the derivative data set and the current model. This map revealed the location of a mercury atom at a single site, close to Cys433. The position of this mercury was refined using the program MLPHARE to provide phase information for the crystal to 3.6 Å. The initial phases set had a FOM of 0.24 and provided useful phases to 3.6 Å resolution. Phase combination using the structure of Ad12 knob and the experimental SIR phases followed by solvent flattening using DM resulted in a map with a FOM of 0.74 to 2.6 Å resolution. Continuous density corresponding to a single domain of CAR was clearly visible in this map. A polyalanine model was built into the density, followed by a cycle of simulated annealing to 3000 K using the program CNS. The resultant SIGMAA-weighted map allowed the side chains to be built unambiguously. Subsequent rounds of model rebuilding and refinement reduced the R factor to 22.5 ($R_{free}$ 24.9%). The current model contains residues 394–578 of the Knob molecule, residues 22–144 of the CAR-D1 and 70 water molecules, with good overall geometry (RMS deviation on bond lengths and bond angles is 0.010 Å and 1.71° respectively). Based on an interrogation of the DALI database (Holm et al., *Science* 273: 595–603 (1996)), the structure of CAR-D1 most closely resembles that of the extracellular domain of the myelin adhesion molecule (Shapiro et al., *Neuron.* 17: 435–449 (1996)), followed by domain 1 of human CD4, a receptor for HIV (Ryu et al., *Structure* 2: 59–74 (1994)), and several other cell surface glycoproteins. Although all of these molecules share a common fold, there are large differences in strand lengths and loop conformations when equivalent atoms are superimposed.

Mutational Analysis. The Ad12 knob mutants listed in Table 2 were constructed by primer-directed PCR mutagenesis and confirmed by nucleotide sequence analysis. Mutant knob proteins were purified as described previously (Freimuth et al., *J. Virol.* 73: 1392–8 (1999)), and were then immobilized on nitrocellulose membranes and incubated with biotinylated CAR-D1 to examine the effect of mutations on knob CAR-D1-binding activity. Purified mutant or wild-type his-tagged knob proteins were bound to nitrocellulose membranes using a dot-blot manifold (5 μg per dot). The membrane was then fixed in 0.25% glutaraldehyde in phosphate-buffered saline (PBS), blocked in 5% milk-PBS, and then incubated sequentially with 5 μg/ml biotinylated CAR-D1 protein, 1:500 horse-radish peroxidase (HRP)-conjugated mouse-anti-biotin monoclonal antibody (Sigma Chemical Co.) (both reagents diluted in 0.5% milk-PBS), and finally with chemiluminescent substrate (SuperSignal, Pierce), with several PBS washes between each incubation. Chemiluminescence was detected on x-ray film, and relative signal intensities were visually assessed. CAR-D1 was biotinylated with sulfo-NHS-LC biotin (Pierce) according to the protocol recommended by the manufacturer. A duplicate membrane containing the same set of knob proteins was incubated with rabbit anti-Ad12 knob serum and then HRP-goat-anti-rabbit IgG (Cappel) followed by chemiluminescent detection to demonstrate that equal amounts of knob protein were present in each dot. All proteins were assayed in duplicate, and the same results were obtained in 3 successive experiments.

TABLE 1

Summary of data collection statistics

|  | Knob | Knob + CAR-D1 | Knob + CAR Thimerosal |
|---|---|---|---|
| Resolution (Å) | 30–2.6 | 30–2.6 | 30–3.4 |
| R merge (%) | 10.0 (22.4) | 7.0 (34.6) | 9.8 (23.6) |
| Completeness (%) | 100.0 (100) | 100.0 (100) | 99.6 (99.7) |
| I/σI | 10 (3) | 20 (6) | 12 (5) |
| Phasing Power |  |  | 1.1 |

TABLE 2

The effect of structure-based substitutions on CAR-D1 binding.

| SUBSTITUTION | POSITION IN KNOB | BIND TO CAR-D1 |
|---|---|---|
| L430A | B strand, R-Sheet | ++ |
| V466Y | D strand, R-Sheet | +++ |
| H467K | D strand, R-Sheet | +++ |
| V469E | D strand, R-Sheet | +++ |
| T543R | H strand, R-Sheet | +++ |
| K545E | H strand, R-Sheet | +++ |
| K545M | H strand, R-Sheet | +++ |
| T560R | I strand, R-Sheet | +++ |
| S564R | I strand, R-Sheet | +++ |
| P417E/P418A | AB loop | − |
| Ins TI 421 | AB loop | − |
| ΔE425/L426 | AB loop | − |
| E425S | AB loop | ++ |
| ΔG550/I551 | HI loop | + |

TABLE 3

Comparison of AB Loop amino acid sequences of CAR-D1 binding adenovirus sub-groups with non-CAR-D1 binding adenovirus sub-groups

| CAR-D1-binding? | Adenovirus Type | AB loop sequence | Sub-Group | SEQ ID NO. |
|---|---|---|---|---|
| Yes | Ad12 | TLWTTPDPP-PNCSLIQE | A | 10 |
| Yes | Ad2 | TLWTTPAPS-PNCRIHSD | C | 11 |
| Yes | Ad9 | TLWTTPDTS-PNCKIDQD | D | 12 |
| Yes | Ad4 | TLWTTPDPS-PNCQILAE | E | 13 |
| Yes | Ad40 Long | TLWTTADPS-PNATFYES | FL | 14 |
| No | Ad40 Short | TIWSI-SPT-PNCSIYET | FS | 15 |
| No | Ad3 | TLWTGVNPTTANCIIEYG | B | 16 |

The invention claimed is:

1. A mutant CAR-D1-binding adenovirus, the mutant adenovirus having a genome comprising one or more mutations in sequences which encode the AB loop of the fiber protein knob domain wherein the mutation in said sequences causes a viral particle encoded by the genome to have a significantly weakened binding affinity for CAR-D1 relative to a wild-type CAR-D1-binding adenovirus, the mutations being selected from the group consisting of substitution of two amino acids, an insertion of one or two amino acids, or a deletion of one or two amino acids, or combinations thereof.

2. The mutant adenovirus of claim 1 which is adenovirus serotype 2.

3. The mutant adenovirus of claim 1 which is adenovirus serotype 12.

4. The mutant adenovirus of claim 1 wherein the binding affinity for CAR-D1 is undetectable.

5. The mutant adenovirus of claim 1 wherein the binding affinity for CAR-D1 is significantly weakened such that it cannot be propagated in natural infections in humans.

6. The mutant adenovirus of claim 1 which is adenovirus serotype 5.

7. The mutant adenovirus of claim 2 wherein the mutation results in substitution of the sequence S408-P409 with the sequence Thr-Thr-Ala.

8. The mutant adenovirus of claim 2 wherein the mutation results in amino acid substitutions S408E and P409A.

9. The mutant adenovirus of claim 3 wherein the mutation results in substitution of the sequence P417–P418 with the sequence Thr-Thr-Ala.

10. The mutant adenovirus of claim 3 wherein the mutation is selected from the group consisting of amino acid substitutions P417E and P418A, insertion of the sequence Thr-Ile between residues 421 and 422, deletion of residues E425 and L426, substitution of the sequence P417–P418 with the sequence Thr-Thr-Ala, or combinations thereof.

11. A mutant CAR-D1-binding adenovirus having a genome comprising one or more mutations in sequences which encode the HI loop of the fiber protein knob domain, wherein the mutation in said sequences causes a viral particle encoded by the genome to have a significantly weakened binding affinity for CAR-D1 relative to a wild type CAR-D1-binding adenovirus.

12. The mutant adenovirus of claim 11 wherein the mutation results in a deletion of amino acids.

13. The mutant adenovirus of claim 11 which is Adenovirus serotype 2.

14. The mutant adenovirus of claim 11 which is Adenovirus serotype 5.

15. The mutant adenovirus of claim 11 wherein the binding affinity for CAR-D1 is undetectable.

16. The mutant adenovirus of claim 11 wherein the binding affinity for CAR-D1 is significantly weakened such that it cannot be propagated in natural infections in humans.

17. The mutant adenovirus of claim 12 wherein the mutation results in a deletion of up to seven amino acids.

18. The mutant adenovirus of claim 17 wherein the mutation results in a deletion of two amino acids.

19. The mutant adenovirus of claim 17 which is adenovirus serotype 2.

20. The mutant adenovirus of claim 17 which is adenovirus serotype 5.

21. The mutant adenovirus of claim 18 which is Adenovirus serotype 12.

22. The mutant adenovirus of claim 21 wherein the mutation results in a deletion of amino acids G550 and I551 of the encoded HI loop of the fiber protein knob domain.

23. A mutant CAR-D1-binding adenovirus serotype 5, wherein the mutant has a significantly weakened binding affinity for CAR-D1 relative to a wild-type CAR-D1-binding adenovirus serotype 5 and wherein the mutation results in the substitution of the sequence S408-P409 with the sequence Thr-Thr-Ala.

24. The mutant adenovirus of claim 6 wherein the mutation results in substitution of the sequence S408-P409 with the sequence Thr-Thr-Ala.

\* \* \* \* \*

SEQUENCE LISTING

<160> NUMBER OF SEQ ID NOS: 16

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Cloning
      vector encoded sequences

<400> SEQUENCE: 1

Leu Glu Asp Pro Ala Ala Asn Lys Ala Arg Lys Glu Ala Glu Leu Ala
1               5                   10                  15

Ala Ala Thr Ala Glu Gln
            20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 2
catatgagca acactccata cg                                         22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 3
ggatccttat tcttgggtaa tgt                                        23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 4
ccatgggtat cactactcct gaagaga                                    27

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 5
ctcgagcgca cctgaaggct ta                                         22

<210> SEQ ID NO 6
<211> LENGTH: 21
<212> TYPE: DNA
<213> ORGANISM: Artificial Sequence
<220> FEATURE:

```
<223> OTHER INFORMATION: Description of Artificial Sequence:
      Cloning Primer

<400> SEQUENCE: 6
ctcgagtgaa ggagggacaa c                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 7
catatgggta tcactactc                                                 19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 8
ggatcctacg cacctgaagg ct                                             22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      Cloning Primer

<400> SEQUENCE: 9
ggatcctatc cagctttatt tgaag                                          25

<210> SEQ ID NO 10
<211> LENGTH: 17
<212> TYPE: PRT
<213> ORGANISM: Adenovirus Type 12

<400> SEQUENCE: 10

Thr Leu Trp Thr Thr Pro Asp Pro Pro Asn Cys Ser Leu Ile Gln
1               5                   10                  15

Glu

<210> SEQ ID NO 11
<211> LENGTH: 17
<212> TYPE: PRT
<213> ORGANISM: Adenovirus Type 5

<400> SEQUENCE: 11

Thr Leu Trp Thr Thr Pro Ala Pro Ser Pro Asn Cys Arg Ile His Ser
1               5                   10                  15

Asp

<210> SEQ ID NO 12
<211> LENGTH: 17
<212> TYPE: PRT
<213> ORGANISM: Adenovirus Type 9

<400> SEQUENCE: 12
```

```
Thr Leu Trp Thr Thr Pro Asp Thr Ser Pro Asn Cys Lys Ile Asp Gln
1               5                   10                  15

Asp

<210> SEQ ID NO 13
<211> LENGTH: 17
<212> TYPE: PRT
<213> ORGANISM: Adenovirus Type 4

<400> SEQUENCE: 13

Thr Leu Trp Thr Thr Pro Asp Pro Ser Pro Asn Cys Gln Ile Leu Ala
1               5                   10                  15

Glu

<210> SEQ ID NO 14
<211> LENGTH: 17
<212> TYPE: PRT
<213> ORGANISM: Adenovirus Type 40 Long

<400> SEQUENCE: 14

Thr Leu Trp Thr Thr Ala Asp Pro Ser Pro Asn Ala Thr Phe Tyr Glu
1               5                   10                  15

Ser

<210> SEQ ID NO 15
<211> LENGTH: 16
<212> TYPE: PRT
<213> ORGANISM: Adenovirus Type 40 Short

<400> SEQUENCE: 15

Thr Ile Trp Ser Ile Ser Pro Thr Pro Asn Cys Ser Ile Tyr Glu Thr
1               5                   10                  15

<210> SEQ ID NO 16
<211> LENGTH: 18
<212> TYPE: PRT
<213> ORGANISM: Adenovirus Type 3

<400> SEQUENCE: 16

Thr Leu Trp Thr Gly Val Asn Pro Thr Thr Ala Asn Cys Ile Ile Glu
1               5                   10                  15

Tyr Gly
```